US009777322B2

(12) United States Patent
Van Eijk et al.

(10) Patent No.: US 9,777,322 B2
(45) Date of Patent: Oct. 3, 2017

(54) SEQUENCE BASED GENOTYPING BASED ON OLIGONUCLEOTIDE LIGATION ASSAYS

(75) Inventors: Michael Josephus Theresia Van Eijk, Wageningen (NL); René Cornelis Josephus Hogers, Wageningen (NL)

(73) Assignee: Keygene N.V., Wageningen (NL)

( * ) Notice: Subject to any disclaimer, the term of this patent is extended or adjusted under 35 U.S.C. 154(b) by 0 days.

(21) Appl. No.: 14/131,181

(22) PCT Filed: Jul. 9, 2012

(86) PCT No.: PCT/NL2012/050493
§ 371 (c)(1),
(2), (4) Date: Apr. 17, 2014

(87) PCT Pub. No.: WO2013/009175
PCT Pub. Date: Jan. 17, 2013

(65) Prior Publication Data
US 2014/0221217 A1    Aug. 7, 2014

Related U.S. Application Data

(60) Provisional application No. 61/505,787, filed on Jul. 8, 2011.

(51) Int. Cl.
| C12Q 1/68 | (2006.01) |
|---|---|
| C12P 19/34 | (2006.01) |
| C07H 21/02 | (2006.01) |
| C07H 21/04 | (2006.01) |
| C40B 50/16 | (2006.01) |
| C40B 50/18 | (2006.01) |

(52) U.S. Cl.
CPC ........... *C12Q 1/6874* (2013.01); *C12Q 1/683* (2013.01); *C12Q 1/6827* (2013.01)

(58) Field of Classification Search
USPC ............ 435/6.1, 6.12, 91.2, 91.52; 536/23.1, 536/24.2, 24.33; 506/16, 31, 32
See application file for complete search history.

(56) References Cited

U.S. PATENT DOCUMENTS

| 4,988,617 A | 1/1991 | Landegren et al. |
|---|---|---|
| 5,470,705 A | 11/1995 | Grossman et al. |
| 5,521,065 A | 5/1996 | Whiteley et al. |
| 5,876,924 A | 3/1999 | Zhang et al. |
| 5,962,223 A | 10/1999 | Whiteley et al. |
| 6,027,889 A | 2/2000 | Barany et al. |
| 6,156,178 A | 12/2000 | Mansfield et al. |
| 6,221,603 B1 | 4/2001 | Mahtani |
| 8,460,866 B2 * | 6/2013 | Van Eijk .............. C12Q 1/6827 435/6.1 |
| 2003/0032016 A1 | 2/2003 | Barany et al. |
| 2003/0108913 A1 | 6/2003 | Schouten |
| 2003/0119004 A1 | 6/2003 | Wenz et al. |
| 2003/0190646 A1 | 10/2003 | Wenz et al. |
| 2006/0211000 A1 * | 9/2006 | Sorge .................. C12Q 1/6809 435/6.14 |

FOREIGN PATENT DOCUMENTS

| EP | 0 185 494 | 6/1986 |
|---|---|---|
| EP | 0 246 864 B1 | 11/1987 |
| EP | 0 745 140 | 12/1996 |
| EP | 0 912 761 | 5/1999 |
| EP | 0 956 359 | 11/1999 |
| EP | 0 964 704 | 12/1999 |
| EP | 1 194 770 | 4/2002 |
| EP | 1 252 334 | 10/2002 |
| EP | 1 255 871 | 11/2002 |
| EP | 1 313 880 | 5/2003 |
| NL | WO 2007/073165 | * 6/2007 |
| WO | WO-96/15271 | 5/1996 |
| WO | WO-97/45559 | 12/1997 |
| WO | WO-98/04745 | 2/1998 |
| WO | WO-98/04746 | 2/1998 |
| WO | WO-03/033722 A2 | 4/2003 |
| WO | WO-03/052142 | 6/2003 |
| WO | WO-03/054511 | 7/2003 |
| WO | WO-03/060163 A2 | 7/2003 |
| WO | WO-2004/111271 | 12/2004 |
| WO | WO-2005/021794 A2 | 3/2005 |
| WO | WO-2005/026389 A2 | 3/2005 |

(Continued)

OTHER PUBLICATIONS

Deschamps et al, Utilization of next-generation sequencing platforms in plant genomics and genetic variant discovery, 2010, Mol. Breeding, 25,553-570 published on Dec. 5, 2009.*
Nilsson, et al. "Padlock Probes: Circularizing Oligonucleotides for Localized DNA Detection", Science, 1994, vol. 265, pp. 2085-2088.
Nilsson, et al., "Making Ends Meet in Genetic Analysis Using Padlock Probes", Human Mutation, 2002, vol. 19, pp. 410-415.

(Continued)

*Primary Examiner* — Narayan Bhat
(74) *Attorney, Agent, or Firm* — Foley & Lardner LLP

(57) ABSTRACT

The invention relates to a method for the detection of a target nucleotide sequence in a sample based on an oligonucleotide ligation assay wherein probes are used that contain (a combination of) sequence-based identifiers that can identify the sample and the target sequence (i.e. locus and/or allele combination) wherein after the ligation step, the ligated probes, or after amplification, the amplified ligated probes, are restricted using restriction enzymes to cut of part of the probes and continue with those parts (identifiers and target sequence) that contain the relevant information in the sequencing step.

22 Claims, 6 Drawing Sheets

(56) References Cited

FOREIGN PATENT DOCUMENTS

| WO | WO-2005/118847 | 12/2005 |
| WO | WO-2007/100243 A1 | 9/2007 |

OTHER PUBLICATIONS

Van Eijk, et al., "SNPWave TM: a flexible multiplexed SNP genotyping technology", Nucleic Acids Research, 2004 (published online Mar. 5, 2004), vol. 32, No. 4, p. e47.
International Search Report received in PCT/NL2012/050493 dated Oct. 2, 2012.

* cited by examiner

FIG 4
FIG 4A
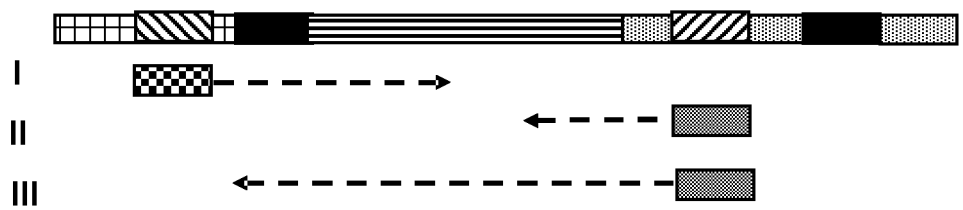
FIG 4B
FIG 4C
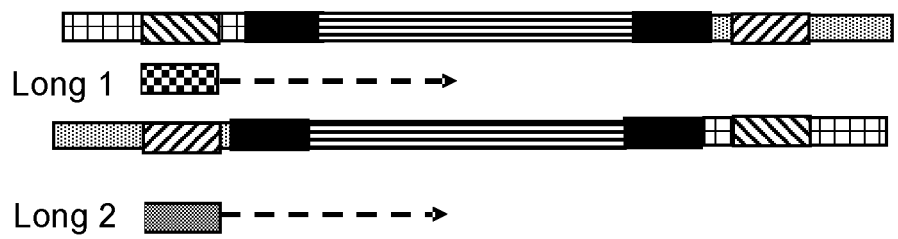
FIG 4D
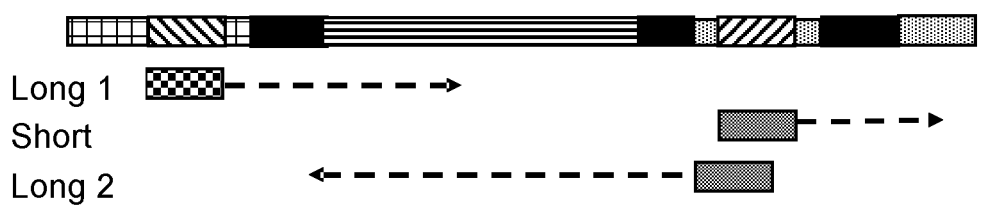

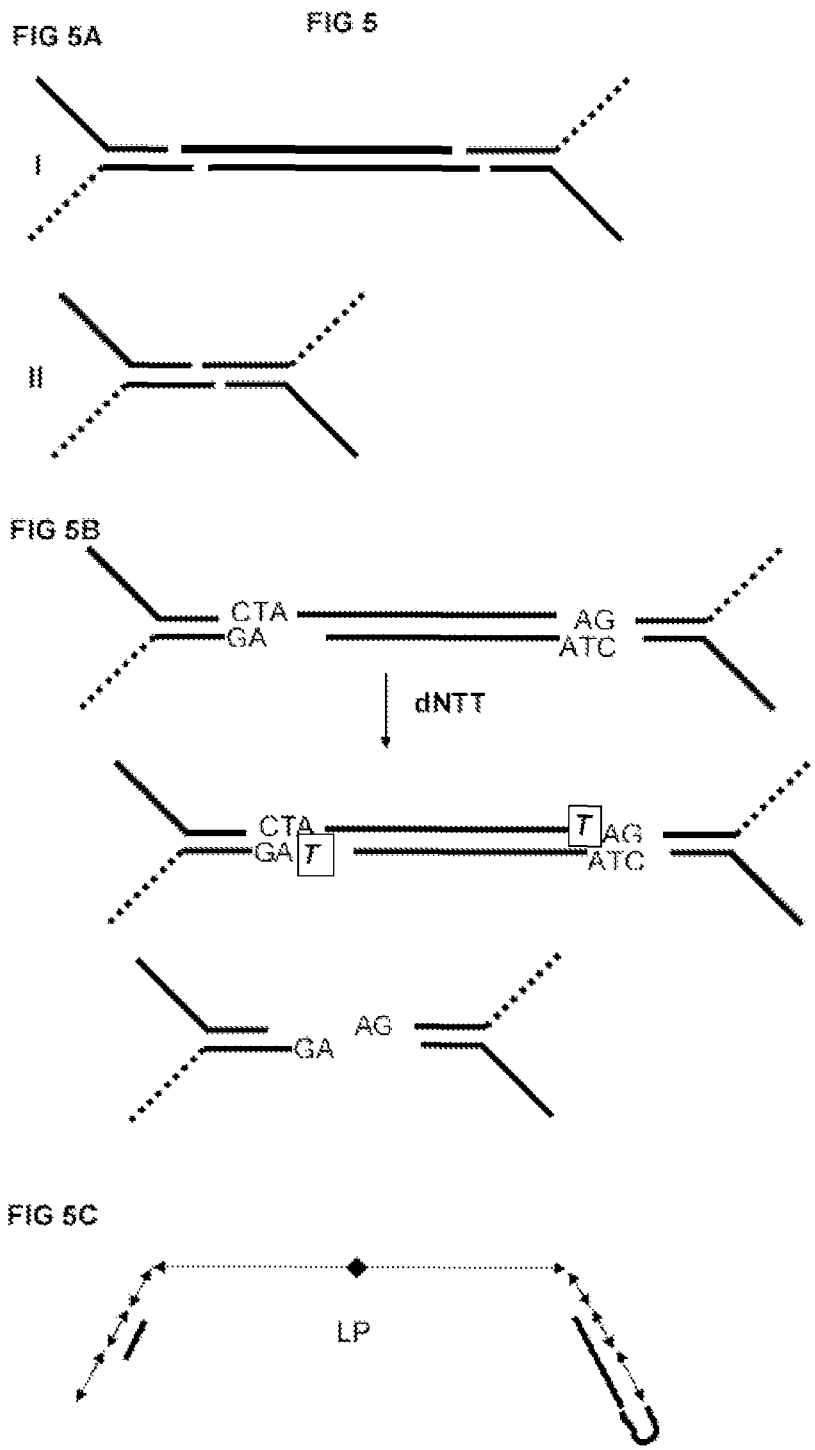

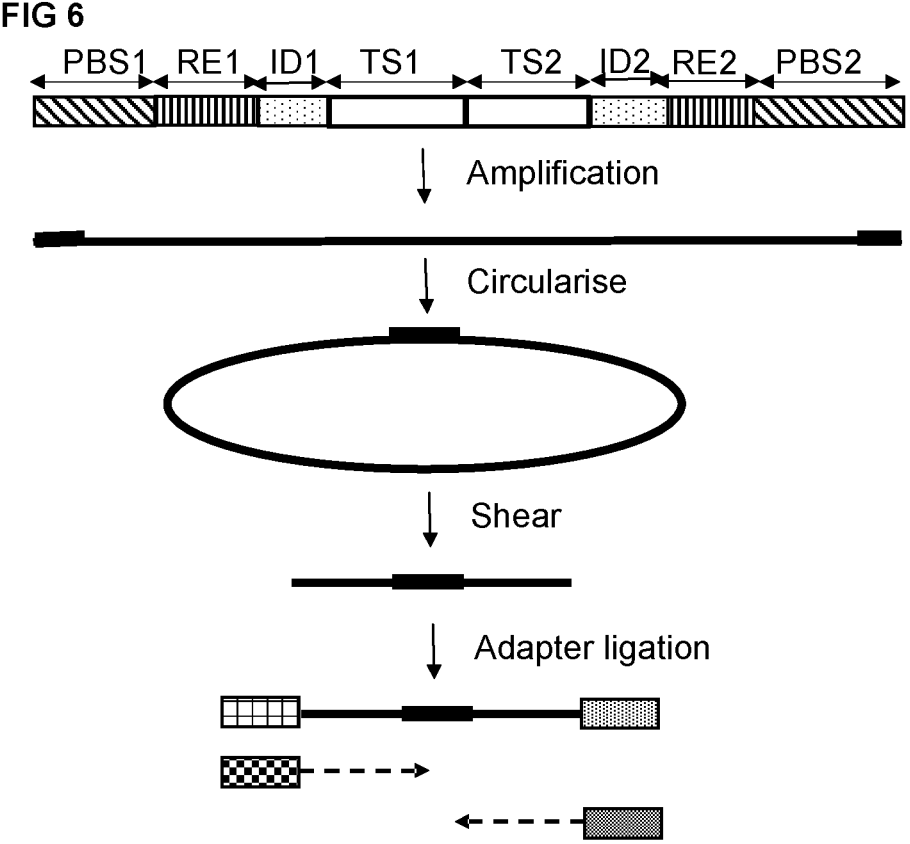

SEQUENCE BASED GENOTYPING BASED ON OLIGONUCLEOTIDE LIGATION ASSAYS

CROSS-REFERENCE TO RELATED APPLICATION

This application is the National Phase of International Patent Application No. PCT/NL2012/050493, filed Jul. 9, 2012, published in English as WO 2013/009175, which claims priority to U.S. Provisional Application No. 61/505,787, filed Jul. 8, 2011. The contents of these applications are herein incorporated by reference in their entirety.

FIELD OF THE INVENTION

The present invention relates to the field of molecular biology and biotechnology. In particular the invention relates to the field of nucleic acid detection, more in particular to the design and composition of (collections) of probes that can be used for the high throughput detection of nucleic acids. The invention also relates to methods for the detection of nucleic acids using the probes and compositions. The invention further provides for probes that are capable of hybridising to a target sequence of interest, primers for the amplification of ligated probes, use of these probes and primers in the identification and/or detection of nucleotide sequences that can be related to a wide variety of genetic traits and genes. The invention further provides kits of primers and/or probes suitable for use in the method according to the invention. The invention finds applicability in the field of the high throughput detection of target nucleotide sequences in samples, whether from artificial, plant, animal or human origin or combinations thereof. The invention finds particular application in the field of high throughput genotyping.

BACKGROUND OF THE INVENTION

With the near exponential increment of genetic information becoming available due to the development of advanced technologies for obtaining information on traits, alleles and sequencing, there is a growing need for efficient, reliable, scalable assays to test samples and in many cases multiple samples in a rapid, often parallel fashion. In particular single nucleotide polymorphisms (SNPs) contain valuable information on the genetic make up of organisms and the detection thereof is a field that has attracted a lot of interest and innovative activity.

One of the principal methods used for the analysis of the nucleic acids of a known sequence is based on annealing two probes to a target sequence and, when the probes are hybridised adjacently to the target sequence, ligating the probes. Detection of a successful ligation event is then indicative for the presence of the target sequence in the sample. The Oligonucleotide Ligation Assay (OLA) is a technology that has been found suitable for the detection of such single nucleotide polymorphisms and has over the years been described in many variations in a number of patent applications and scientific articles.

The OLA-principle (Oligonucleotide Ligation Assay) has been described, amongst others, in U.S. Pat. No. 4,988,617 (Landegren et al.). This publication discloses a method for determining the nucleic acid sequence in a region of a known nucleic acid sequence having a known possible mutation or polymorphism. To detect the mutation, oligonucleotides are selected to anneal to immediately adjacent segments of the sequence to be determined. One of the selected oligonucleotide probes has an end region wherein one of the end region nucleotides is complementary to either the normal or to the mutated nucleotide at the corresponding position in the known nucleic acid sequence. A ligase is provided which covalently connects the two probes when they are correctly base paired and are located immediately adjacent to each other. The presence, absence or amount of the linked probes is an indication of the presence of the known sequence and/or mutation. Other variants of OLA-based techniques have been disclosed inter alia in Nilsson et al. Human mutation, 2002, 19, 410-415; Science 1994, 265: 2085-2088; U.S. Pat. No. 5,876,924; WO 98/04745; WO 98/04746; U.S. Pat. No. 6,221,603; U.S. Pat. No. 5,521,065; U.S. Pat. No. 5,962,223; EP 185494BI; U.S. Pat. No. 6,027,889; U.S. Pat. No. 4,988,617; EP 24686481; U.S. Pat. No. 6,156,178; EP 745140 BI; EP 964704 BI; WO 03/054511; US 2003/0119004; US 2003/190646; EP 1313880; US2003/0032016; EP 912761; EP 956359; US 2003/108913; EP 1255871; EP 1194770; EP 1252334; WO96/15271; WO97/45559; US2003/0119004A1; U.S. Pat. No. 5,470,705.

Further advancements in the OLA techniques have been reported by KeyGene, Wageningen, the Netherlands. In WO 2004/111271, WO2005/021794, WO2005/118847 and WO03/052142, they have described several methods and probe designs that improved the reliability of oligonucleotide ligation assays. These applications further disclose the significant improvement in multiplex levels that can be achieved. Also "SNPWave: a flexible multiplexed SNP genotyping technology". van Eijk M J, Broekhof J L, van der Poet H J, Hogers R C, ..., Geerlings H, Buntjer J B, van Oeveren A J, Vos P Nucleic Acids Res. 2004; 32(4):e47) describes the improvements made in this field.

With the onset of Next Generation Sequencing (NGS) technologies such as described in Janitz Ed. Next Generation Genome sequencing, Wiley VCH, 2008 and available on the market in platforms provided for by Roche (GS FLX and related systems) and Illumina (Genome Analyzer and related systems), the need arose to adapt the OLA assay to sequencing as a detection platform. Improvements in that field have been described inter alia in WO 2007100243 of Keygene Nev. In WO2007100243, the application of next generation sequencing technology to the results of oligonucleotide ligation assays have been described. There remains a need for further improvements in this field, not only from the point of, reliability and accuracy, but also from economic drivers to further reduce the costs by increasing scale.

There is a continuing need for oligonucleotide probes that combine the advantages and avoid the specific disadvantages of the various ligation probe types and detection methods known in the art. There is also a need for further improvement of the technology by providing probes that have additional advantages. It is one of the goals of the present invention to provide such probes and methods. It is another goal of the present invention to avoid the disadvantages of the commonly known probes as mentioned hereinbefore. It is a further goal of the invention to provide for probes that are suitable for high throughput detection methods. It is also a goal of the present invention to provide for an efficient, reliable and/or high throughput method for the detection of target nucleotide sequences by performing oligonucleotide ligation assays. The present inventors have set out to eliminate or at least diminish the existing problems in the art while at the same time attempting to maintain the many advantageous aspects thereof, and to further improve the technology. Other problems in the art and solutions provided thereto by the present invention will become clear throughout the description, the figures and the various embodiments described herein.

BRIEF DESCRIPTION OF THE DRAWINGS

The present invention is illustrated by the following figures:

In FIG. 1, different probe types (FIG. 1A, FIG. 1B, FIG. 1C) are schematically illustrated vis-à-vis a target nucleotide sequence (T) of interest. Various components of the probes have been depicted, using identical depictions throughout the figure.

FIG. 1A illustrates a general oligonucleotide ligation assay based on a linear probe type directed to a target sequence (T), wherein a first probe (P1) comprises a first target specific section (TS1) and a first tag section (TAG1) comprising a first identifier (ID1) and a first primer binding sequence (PBS1), capable of annealing to a first primer (PR1). A second probe (P2) comprises a second target specific section (TS2) and a second tag section (TAG2) comprising an optional second identifier (ID2) and a second primer binding sequence (PBS2), capable of annealing to a second primer (PR2). In embodiments for allele specific detection, TS2 may contain, preferably at its 3'-end, an allele specific nucleotide, preferably together with a different identifier (ID2) in the tag section. In other embodiments for allele specific detection, TS1 may contain, preferably at its 5' end, an allele specific nucleotide, preferably together with a different identifier (ID1) in the tag section. The locus-allele combination may then be determined (genotyped) by detection of the presence or absence of ID1 and/or ID2. In similar manner, all allelic variants of a polymorphism can be genotyped (for example, 2 alleles of a bi-allelic polymorphisms using two probes with each an allele-specific target section or for 4 alleles, using 4 allele-specific target sections). When detection is based on sequencing, the detection of the presence, absence or amount can also be based on the sequence information from the ligated probes by a combination of identifiers and sequence information from the target specific section. So, the allele can be determined via sequencing of (part of the target section itself whereas the locus can be determined by sequencing of the identifier and vice versa).

FIG. 1B illustrates an oligonucleotide ligation assay according to the invention based on a linear probe type directed to a target sequence (T). The probes have now been equipped with a recognition sequence for a restriction endonuclease (RE1, RE2).

FIG. 1C illustrates an oligonucleotide ligation assay according to the invention based on a linear probe type directed to a target sequence (T). The probes have now been equipped with a recognition sequence for a restriction endonuclease (RE1, RE2) and identifiers (ID1, ID2).

FIG. 3 illustrates a schematic representation of a number of elements that are present in several embodiments of the invention. For ease of reference they have been linked to the earlier used indications. Thus, TS represents a target specific section, ID indicates an identifier, RE a recognition sequence for a restriction endonuclease. A primer binding site is indicated as PBS. An adapter that is ligated to a restricted fragment is depicted as AD. Primers used in the amplification step (whether for amplification as part of library preparation or as part of the sequencing step) are indicated as PR. The restricted amplicons/restricted ligated probes/are indicated as RA/RLA. To indicate that certain elements are used in the sequencing of the method of the invention, this can be indicated by the prefix SEQ. Thus an adapter used in the sequencings step can be indicated as 'sequencing adapter' or SEQ AD. When two or more elements are present at the same time, this indicates a numerical suffix. Thus ID1 is the first identifier, ID2 is the second and so on.

FIG. 4 illustrates various embodiments for the sequencing of the fragments of the invention. As the (amplified) ligated probes have been restricted using the restriction endonucleases, the restricted amplicons/restricted ligated probes are indicated as RA/RLP (and hence contain locus and allele information, L and Al, respectively). After restriction, adapters have been added (AD1, AD2) that may be sequencing adapters (SEQ AD1, SEQ AD2) that can be used in the sequencing step (examples are known on the art as P5/P7 primers (Illumina). Primers used in the sequencing step (sequencing primers) are indicated as SEQ PR1, SEQ PR2 and are complementary to sections (primer binding sequences) in the sequencing adapters.

FIG. 4A illustrates single read sequencing (I) from one end or from the opposite end and paired end sequencing (I and II combined). The sequencing fragment, comprising the RA/RLP and further comprising one or more identifiers (ID, L, Al) is sequenced in one direction (striped arrow), using one sequencing primer leading to (depending on the read length generated by the sequencing platform) a read that identifies the presence/absence or amount of the target sequence by providing the sequence of the identifier and, optionally (part of) the RA/RLP. The read produced by I mainly provides sequence information of the adapter (including the ID), II mainly of the target sequence and III on both, provided the read is long enough, depending on the platform.

FIG. 4B illustrates unidirectional double tagging sequencing. The restricted ligated probe or restricted amplicon (RA/RLP) has been ligated to two sequencing adapters and sequenced in one direction but with two primers (SEQ PR1, SEQ PR2). The two primers result in two different reads, a short read and a long read. Sequencing provides at least sequence information on the identifiers (both for the short read and the long read) and the sequence of (part of) RLP/RA, possibly including L and Al.

FIG. 4C illustrates an embodiment wherein a re-clustering step is performed. The sequencing fragments is sequenced in one direction resulting in the first read (Long1). The sequencing fragment is re-clustered by annealing the other sequencing adapter to the carrier on which the sequencing is performed. The fragment is sequenced from the other end, resulting in another long read (Long 2).

FIG. 4D illustrates an embodiment that is a combination of the embodiment described in FIGS. 4B and 4C. Thus, first a unidirectional double tagging sequencing procedure is followed by re-clustering and sequencing the fragment from the other direction, resulting in a combination of two long reads and a short read.

FIG. 5 illustrates the use of a Y shaped adapter.

FIG. 5A shows a Y-shaped adapter wherein the adapter in the arms of the Y can contain different elements such as identifiers, sequencing adapters, primer binding sites etc. One arm of the Y is hence different from the other arm of the Y. The bottom of the Y-shape is double stranded (i.e. contains complementary strands) and both strands are capable of being ligated to the restriction fragment. This embodiment can be used when only one recognition site has been introduced in both tag sections of the two probes, only one adapter is needed to ligate adapters to both sides of a restriction fragment such as a RLA or a RA (see I). Self ligation of the Y-fork adapter is shown in FIG. 5A II.

FIG. 5B shows how to avoid self-ligation of the Y-shaped adapters as depicted in FIG. 5A (II). The annealing end of the adapter can be designed to ligate only one strand. The other strand has a gap, preventing ligation. This is illustrated by a staggered end at the fragment of CTA, combined with an overhang in the Y-fork of only GA. This prevents self ligation.

FIG. 5C illustrates some of the embodiments of the invention wherein the single strand of the ligated probe is restricted, using an additional oligonucleotide or by ligation of a hairpin probe. Both embodiments provide strands that can be cut by a restriction endonuclease.

FIG. 6 illustrates the method of mate pair sequencing, comprising a circularization step and a step wherein the two ends of the fragment are linked and, after fragmentation and ligation of adapters, are subsequently sequenced together.

SUMMARY OF THE INVENTION

Figure 1:
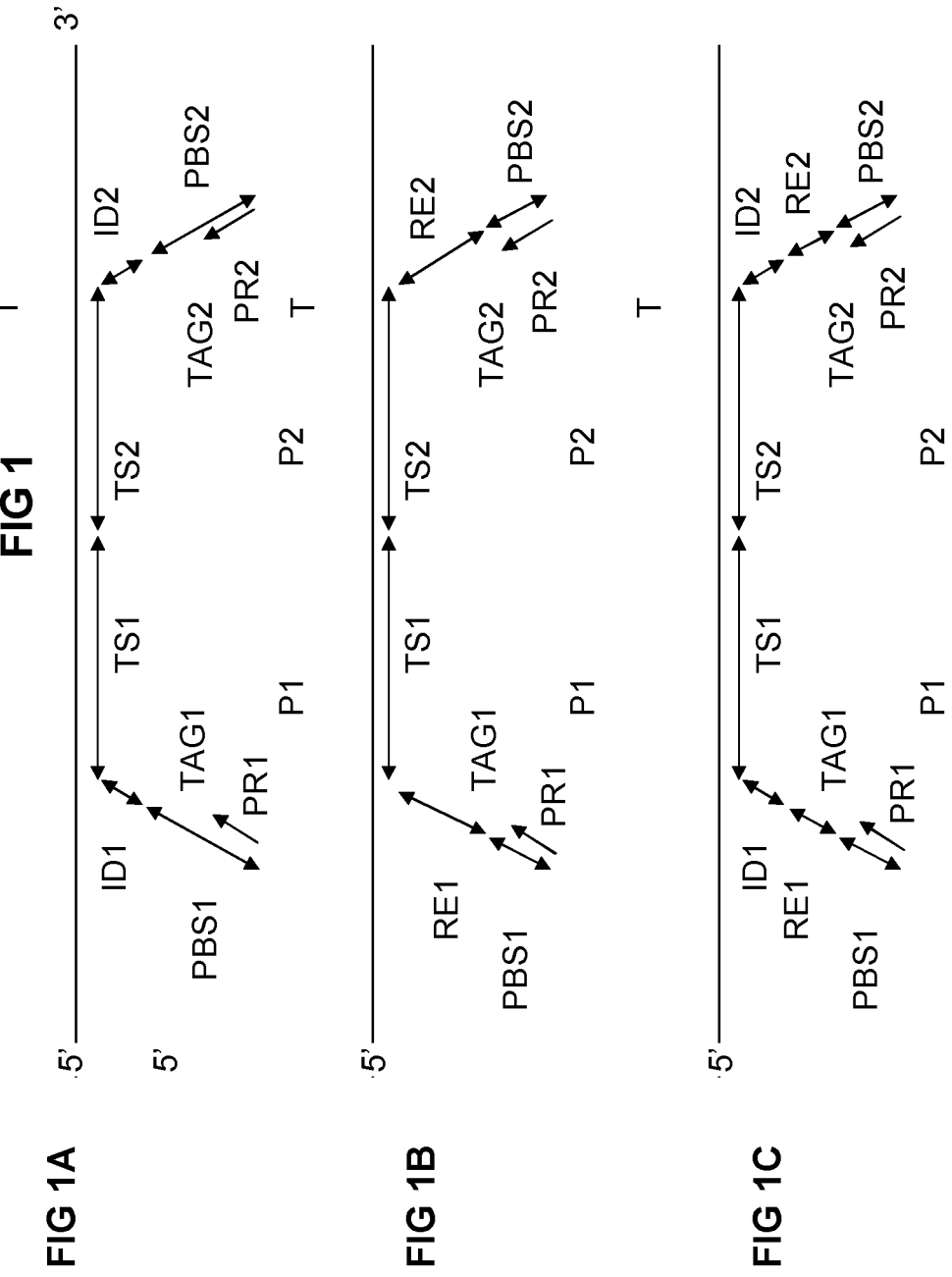
FIG. 1.

The present inventors have been able to combine novel high throughput sequencing technologies with the versatility of oligonucleotide ligation based assays. In particular, the invention relates to a method for high throughput detection of target nucleotide sequences based on oligonucleotide ligation assays, wherein the probes used in the ligation assays are modified such that a high throughput sequencing method can be used to unequivocally reveal the present absence of the amount of the one or more target nucleotide sequences. The inventors have found that improvements can be made by adapting the existing methods to focus on the detection of the parts of the ligation product that are relevant for an adequate detection of the target sequences in a plurality of samples. The method is based on the use of (combinations of) sequence-based identifiers in combination with a step that reduces the amount of non-relevant sequence data by the removal (trimming) of part of the (ligated) probes prior to sequencing. The use of adapters (that may contain identifiers) that are connected to the restricted ligated probes or amplified ligated probes allows the use of generic sets of adapters and identifiers and primers in combination with purposively designed probes for target sequences. The modular approach, separating the elements of the probe that are connected to the target itself and the elements that are connected to the sample multiplexing and sequence based detection allows for an advantageous flexibility in combination with a tested reliability. The invention leads to advantageous methods for high throughput genotyping of large numbers of samples for large numbers of genotypes with high accuracy and low costs per data point. The invention also allows to adapt proven OLA technology to novel detection platforms based on sequencing.

DETAILED DESCRIPTION OF THE INVENTION

The invention in its broadest form relates to a method for the detection of a target nucleotide sequence in a sample based on an oligonucleotide ligation assay wherein probes are used that are provided with or contain (a combination of) sequence-based identifiers that can identify the sample and/or the target sequence (i.e. locus and/or allele combination) wherein after the ligation step, the ligated probes, or after amplification, the amplified ligated probes, are restricted using restriction enzymes to cut off part of the probes, where necessary ligate identifier containing adapters and continue with those parts (identifiers and/or target sequence) that contain the relevant information in the sequencing step for the proper calling of the sample and/or genotype based on the presence and/or absence of identifier(s).

Thus, in more detail, the invention pertains to a method for the determination of a target nucleotide sequence in a sample comprising the steps of (a) providing for each target nucleotide sequence (T) a first probe (P1) and a second probe (P2),
wherein the first probe comprises a first target specific section (TS1) and a first tag section (TAG1) that is non-complementary to the target nucleotide sequence and that optionally comprises a first primer binding sequence (PBS1), wherein the first tag section comprise a first recognition sequence (RE1) for a first restriction endonuclease; wherein the second probe comprises a second target specific section (TS2) and a second tag section (TAG2) that is non-complementary to the target nucleotide sequence and that comprises an optional second primer binding sequence (PBS2), wherein second tag section comprises an optional second recognition sequence (RE2) for a second restriction endonuclease;

(b) allowing the first and second target specific section of the respective first and second probe to hybridize to the target sequence;

(c) ligating the first and second probe when the respective target specific sections of the probes are hybridized to essentially adjacent sections on the target sequence to provide ligated probes (LP);

(d) optionally amplifying the ligated probes with an optional first and/or an optional second primer to provide amplicons (A);

(e) restricting the ligated probes or amplicons with the first and/or second restriction endonuclease to provide restricted ligated probes (RLP) or restricted amplicons (RA), ligating a first and/or a second adapter containing an adapter-based identifier (AD ID1, AD ID2) to the restricted ligated probes (RLP) or restricted amplicons (RA)

(f) subjecting the adapter-ligated restricted ligated probes (RLP) or adapter-ligated restricted amplicons (RA) to high throughput sequencing technology to determine at least part of the nucleotide sequence of the restricted ligated probes or restricted amplicons (g) identifying the presence, absence or amount of the target nucleotide sequence in the sample.

The method starts with the provision of one or more samples (that may be combined or pooled) that may (or is suspected to) contain the target nucleotide sequence (sequence of interest). To this sample, the set (of a first and a second probe) of probes is added (for each target sequence, different sets of probes may be provided) and the target specific sections of the probes are allowed to hybridize to the target sequence under suitable conditions. After hybridization, any probes hybridized essentially adjacent on the target sequence are ligated to result in ligated probes. The ligated probes may be amplified or, alternatively, directly subjected to sequencing using high throughput sequencing methods. With the sequencing step, the presence of the (allele-specific) target sequence in the sample is determined and the genotypes can be determined.

One aspect of the present invention pertains to the advantageous design of the probes used in the present invention. These probes will be discussed in more detail herein below. Another advantageous aspect of the invention resides in the connection between the state of the art high throughput sequencing technologies as a detecting platform for oligonucleotide ligation assays and the discriminatory power of the OLA-based assays. The present inventors have observed that apart from innovations in probe design, also the methods of performing OLA assays in combination with high throughput sequencing requires considerable amendments to both probes and protocols.

In step (a) of the method for each target nucleotide sequence (T) in the sample (S) a set of probes is provided. The set of probes may comprise a first probe (P1) and a second probe (P2).

The first probe comprises a first target specific section (TS1) and a first tag section (TAG1). The first tag section is non-complementary to the target nucleotide sequence, i.e. it is composed of a nucleotide sequence that does not anneal or hybridize to the target sequence under the stringency conditions employed for the annealing of the target sequence specific section. In certain embodiments the first probe comprises a target specific section at its 3'-end. The first tag section may further comprises a first primer binding sequence (PBS1). The first primer binding sequence is capable of binding a primer (PR1).

The second probe comprises a second target specific section (TS2) and a second tag section (TAG2). The second tag section is non-complementary to the target nucleotide sequence, i.e. it is composed of a nucleotide sequence that does not anneal or hybridize to the target sequence under the stringency conditions employed for the annealing of the target sequence specific section. In certain embodiments, the second probe comprises a second target specific section at its 5'-end. The second tag section may further comprise a second primer binding sequence (PBS2). The second primer binding sequence (if present) is capable of binding a primer (PR2).

At least one of the tag sections contains a recognition sequence for a restriction endonuclease. The first and/or the second tag section may comprise, independently, a first and/or a second recognition sequence (RE1, RE2) for a first and/or second restriction endonuclease. The first and the second recognition sequence may be the same or different (i.e. RE1=RE2 or RE1≠RE2) from each other. There is a preference for restriction endonucleases having two different recognition sequences (RE1≠RE2). The recognition sequence is located between the primer binding site (if present) and the target-specific section. The first recognition sequence may be located between the optional first primer binding sequence and the first target-specific section. The second recognition sequence may be located between the second primer binding sequence (if present) and the second target-specific section.

The respective first and second target specific sections of the probes are allowed to hybridise to preferably essentially adjacent sections on the target sequence, although in some embodiments a gap of one or more nucleotides may be present between the two sections (gap ligation, see for instance WO2007/100243, WO00/77260, US5185243, EP439182 and further below).

In certain embodiments, the first and second probes are ligated i.e. connected to each other. The probes are ligated to each other essentially when the respective (first, second) target section are hybridised (or annealed) to essentially adjacent sections on the target sequence.

The ligation of the first and second probe provides for ligated probes (LP).

The ligated probes (LP) are now:

i). restricted with the first and/or second restriction endonuclease that is capable of recognising the first and/or second recognition sequence of the restriction endonuclease to provide restricted ligated probes (RLP) (this may require the use of complementary oligonucleotides and/or hairpin probes or the use of ssDNA-endonucleases, as described herein elsewhere); or ii). amplified (linear or exponential) with a first and/or optional second primer to result in amplicons (A) and then restricted with the first and/or second restriction endonuclease that is capable of recognising the recognition sequence of the restriction endonuclease to provide restricted amplicons (RA).

By treating the ligated probes with one or more restriction endonucleases, the restricted ligated probes have been liberated of parts of the tag section. This significantly reduces the length of the ligated probes and consequently the amount of data produced as well as improves that adaptability of the oligonucleotide ligation assay technology to the use of high throughput sequencing strategies that prefer shorter reads. The restricted ligated probes comprise the remains of the first and/or second recognition sequence of the restriction endonuclease, the first and second target complementary section. The restricted ligated probes may further contain one or more sequence-based identifiers (ID), essentially as explained herein below. To aid in treating the ligated probes with restriction endonucleases, additional oligonucleotides may be provided that can anneal to the ligated probes at the positions of the restriction and/or recognition sites to provide for double stranded restriction and/or recognition sites. Alternatively, hairpin-shaped probes can be ligated to the ligated probes that cover the positions of the restriction and/or recognition sites to provide for double stranded restriction and/or recognition sites that can subsequently be restricted. Alternatively the first and/or probes themselves may contain a hairpin structure to that effect.

The restricted amplicons (or restricted ligated probes) are now subjected to high throughput sequencing technology, essentially as described herein below to determine at least part of the nucleotide sequence of the restricted amplicons or restricted ligated probes. In certain embodiments, at least part of the target specific section is determined. In certain embodiments, where identifiers have been incorporated in the probes, as explained in more detail below, and thus in the restricted ligated probes or restricted amplicons, at least the sequence of one or more of the identifiers is determined. In certain preferred embodiments, a combination of the target specific section (allele and/or locus information) and the one or more identifiers is determined.

By determining the sequence of the identifiers and/or at least part of the target specific section, the presence, absence or amount of the target sequence in the sample is identified.

Target Nucleotide Sequence

In its widest definition, the target sequence may be any nucleotide sequence of interest. The target sequence can be any sequence of which the determination/detection is desired, for instance because it is indicative, associated or representative of a certain ailment or genetic make up or disorder. The target sequence preferably is a nucleotide sequence that contains, represents or is associated with a polymorphism.

As used herein, the term 'polymorphism' refers to the presence of two or more variants of a nucleotide sequence in a population. A polymorphism may comprise one or more base changes, an insertion, a repeat, or a deletion. A polymorphism includes e.g. a simple sequence repeat (SSR) and a single nucleotide polymorphism (SNP), which is a variation, occurring when a single nucleotide: adenine (A), thymine (T), cytosine (C) or guanine (G)—is altered. A variation must generally occur in at least 1% of the population to be considered a SNP. SNPs make up e.g. 90% of all human genetic variations, and occur every 100 to 300 bases along the human genome. Two of every three SNPs substitute Cytosine (C) with Thymine (T). Variations in the DNA sequences of e.g. humans or plants can affect how they handle diseases, bacteria, viruses, chemicals, drugs, etc.

A polymorphic marker or site is the locus at which sequence divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTRs), hypervariable regions, minisatellites, dinucleotide repeats, trinucleotide repeats, tetranucleotide repeats, simple sequence repeats, (elements of) Quantitative Trait Loci, and insertion elements such as Alu. The first identified allelic form is arbitrarily designated as the reference form (wild type) and other allelic forms are designated as alternative or variant alleles. The allelic form occurring most frequently in a selected population is sometimes referred to as the wild type form. Diploid (and tetraploid/hexaploid) organisms may be homozygous or heterozygous for allelic forms. A diallelic polymorphism has two forms. A triallelic polymorphism has three forms. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. Single nucleotide polymorphisms can also arise from a deletion of a nucleotide or an insertion of a nucleotide relative to a reference allele. Other polymorphisms include (small) deletions or insertions of several nucleotides, referred to as indels. The process of analysing the particular genetic variations (polymorphisms) existing in an individual DNA sample using the presently described methods is sometimes referred to in this application as genotyping or SNP genotyping in the ace of single nucleotide polymorphisms. The method of the present invention allows for co-dominant genotyping using a set of probes for each allele. This embodiment is advantageous in the case of heterozygous samples.

As used herein, the term "allele(s)" means any of one or more alternative forms of a gene at a particular locus. In a diploid cell of an organism, alleles of a given gene are located at a specific location, or locus (loci plural) on a chromosome. One allele is present on each chromosome of the pair of homologous chromosomes. A diploid, or plant species may comprise a large number of different alleles at a particular locus. The locus of a wild type accessions may, thus, comprise various alleles, which may vary slightly in nucleotide and/or encoded amino acid sequence.

As used herein, the term "locus" (loci plural) means a specific place or places or a site on a chromosome where for example a gene or genetic marker is found. For example, the "locus" refers to the position in the genome where the gene (and corresponding alleles) is (are) found.

Sample

A sample can contain at least one target sequence and in principle the method of the present invention can be executed on one sample containing one target sequence ('single sample-monoplex'). It is preferred that a sample contains two or more different target sequences ('single sample—multiplex'), i.e. two or more refers to the identity rather than the quantity of the target sequences in the sample. In particular, the sample comprises at least two different target sequences, in particular at least 100, preferably at least 250, more preferably at least 500, more in particular at least 1000, preferably at least 2500, more preferably at least 5000 and most preferably at least 10000 additional target sequences. In practice, the number of target sequences in a sample that can be analysed is limited, among others, by the number of amplicons or ligated probes than can be detected. The presently employed detection methods allow for relative large numbers of target sequences. The sample can be directly isolated from an individual or group of individuals or can be derived therefrom, such as cDNA, plasmids, YACs, BACs, cosmids, libraries of artificial chromosomes etc.

Plurality of Samples

In certain embodiments, a plurality of samples can be analysed using the method of the invention. Each sample can be derived from a different origin, for instance, different patients that have to be screened for the presence or absence of certain genetic dispositions for certain ailments. Or samples can be derived from the progeny of a crossing to screen for different polymorphisms. The present method can be used to analyse at least two different samples, in particular at least 100, preferably at least 250, more preferably at least 500, more in particular at least 1000, preferably at least 2500, more preferably at least 5000 and most preferably at least 10000 samples for the absence or presence of one ('monoplex-monoplex') or more or a plurality ('multiplex-multiplex') of target sequences. The samples can be distinguished in the further processing of the method using one or more (combinations of) identifiers as outlined herein elsewhere.

DNA

In the (nucleic acid) sample, nucleic acids comprising the target nucleotide sequence may be any nucleic acid of interest. Even though the nucleic acids in the sample will usually be in the form of DNA, the nucleotide sequence information contained in the sample may be from any source of nucleic acids, including e.g. RNA, polyA+ RNA, cDNA, genomic DNA, organellar DNA such as mitochondrial or chloroplast DNA, synthetic nucleic acids, DNA libraries (such as BAC libraries/pooled BAC clones), clone banks or any selection or combinations thereof. The DNA in the sample may be double stranded, single stranded, and double stranded DNA denatured into single stranded DNA. Denaturation of double stranded sequences yields two single stranded fragments, one or both of which can be analysed by probes specific for the respective strands. Preferred nucleic acid samples comprise target sequences on cDNA, genomic DNA, restriction fragments, adapter-ligated restriction fragments, amplified adapter-ligated restriction fragments, AFLP® fragments or fragments obtained in an AFLP-template pre-amplification.

Probe

The sections of the oligonucleotide probes that are complementary to the target sequence are designed such that for each target sequence in a sample, a pair of a first and a second probe is provided, whereby the probes each contain a section at their extreme end that is complementary to a part of the target sequence (a first and a second part of the target sequence, respectively) and the corresponding complementary parts of the target sequence are preferably located essentially adjacent to each other.

In certain embodiments, additional first and/or second probes can be provided, corresponding to different alleles of a locus. In certain embodiments, the allele specific nucleotide is located at the position of either the first or the second probe at which ligation is to occur, i.e. at the end of the target specific section.

In certain embodiments, within a pair of oligonucleotide probes, the first oligonucleotide probe has a section at its (phosphorylated) 5'-end that is complementary to a first part of a target sequence and the second oligonucleotide probe has a section at its 3'-(hydroxyl) end that is complementary to a second part of the target sequence. Thus, when the pair of probes is annealed to complementary parts of a target sequence, the 5'-end of the first oligonucleotide probe is essentially adjacent to the 3'-end of the second oligonucleotide probe such that the respective ends of the two probes may be ligated to form a phosphodiester bond or covalently connect in any other suitable fashion. In certain embodiments, within a pair of oligonucleotide probes, the first oligonucleotide probe has a section at its 3'-end that is complementary to a first part of a target sequence and the second oligonucleotide probe has a section at its 5'-end that is complementary to a second part of the target sequence. Thus, when the pair of probes is annealed to complementary parts of a target sequence, the 3'-end of the first oligonucleotide probe is essentially adjacent to the 5'-end of the second oligonucleotide probe such that the respective ends of the two probes may be ligated to form a phosphodiester bond or covalently connect in an other suitable fashion.

For allele specific detection, it is preferred that the allele-specific probe has its target specific section at the 3' end of the probe. The other way around, the allele specific probe at the 5' end of the probe is less preferred.

In certain embodiments, for each target sequence for which the presence, absence or amount in a sample is to be determined, a specific pair of first and second oligonucleotide probes is designed, each probe with a section complementary to the adjacent complementary part of each target sequence, as described above. Thus, in the method of the invention, for each target sequence that is present in a sample, a ligated probe or a corresponding (specific) amplicon may be obtained in the amplified sample. In certain embodiments, a multiplicity of first and second oligonucleotide probes complementary to a multiplicity of target sequences in a sample is provided. A pair of first and second oligonucleotide probes for a given target sequence in a sample will at least differ in nucleotide sequence from probe pairs for other target sequences or other samples, and may differ in length and/or mass from probe pairs for other targets (although, as outlined above, this is less preferred). More preferably, a probe pair for a given target will produce a ligated probe (sometimes indicated as connected probe) and/or amplicon that differs in sequence from ligated probes and/or amplicons corresponding to other targets in the sample.

There is a number of probe variations possible within the scope of the present invention that can be used as alternatives to the first and second probe (sometimes indicated as 'linear probes') described herein. Examples are so-called padlock probes and key lock probes. These probe variants can be used interchangeably, i.e. combinations of linear, padlock and Keylock probes may be used in one assay.

Padlock Probes

In certain embodiments, of the invention, circularizable probes or padlock probes can be used. The first and second probes are then combined into one probe. The circularizable probe is a linear oligonucleotide that, when annealed to the target sequence, and when ligated, has a circular conformation that is topologically locked to the target sequence. In certain embodiments, an exonuclease treatment of the sample after the ligation step and prior to amplification, preferably PCR-amplification, serves to remove any non-ligated circular probes and to prevent any non-ligated probes from amplification. Circularizable probes are themselves known in the art, for instance from EP745140 or from Van Eijk et al, Nucleic Acids Research, 2004, 32, e47. The known padlock probes are commonly amplified using rolling circle amplification or the polymerase chain reaction resulting in concatamers. Furthermore, the primer binding sites in the known circularizable probes are oriented such that the entire circularized probe is amplified including any target specific sections. In order to circumvent concatamer products during PCR amplification, a blocking modification can be incorporated in the circularizable ligation probe between the two primer binding sites of the type described in WO03/052142. In certain embodiments, the primer binding sites in the present circularizable probes are oriented such that preferably only the section comprising the primer binding sites and the identifier is amplified and preferably the ligated target specific sections are not amplified. Preferably in combination with the exonuclease treatment to remove unligated circularizable probes, this provides amplicons of relatively short length compared to conventional amplicons obtained from conventionally amplifying circularised probes. This avoids the formation of large concatamers and further unnecessary amplification of the entire circularized probe. In certain embodiments, the identifier is located essentially adjacent to one of the primer binding sequences, and preferably between the first and second primer binding site, such that upon amplification the amplicons at least comprises one of the two primer binding sites and the intermittent identifier. The at least one, preferably two recognition site(s) of the restriction endonuclease is/are located preferably such that the recognition sites encompass the first and/or second identifier and the first and second target specific sections of the probe. Subsequent high throughput sequencing of the amplicons or restricted ligated probe will provide the sequence of the identifier and/or (part of) the sequence of the target section(s) and hence of the presence of the target sequence in the sample. In this embodiment, the presence of the recognition sequence for the restriction endonuclease allows the concatamers to be reduced to sequencable fragments.

Keylock Probes

In certain embodiments, for each given target sequence to be detected, preferably at least a pair of two probes is designed such that each probe in the pair is capable of hybridizing to a part of the target sequence and the respective probes in the pair further each comprise a section that is complementary to a corresponding section of the other probe in the pair such that both probes are capable of hybridizing to each other. The two probes in the pair are designed such that when hybridized to each other they are each also capable of hybridizing to a target sequence. When hybridized to each other the two probes mimic or act as padlock probes when used in an oligonucleotide ligation assay for the detection of a target nucleotide sequence, whereas in the subsequent amplification and detection steps the probes function as a linear ligation product. This type of probe has been dubbed "Keylock" and is disclosed inter alia in WO2004111271. In this embodiment, the presence of the recognition sequence for the restriction endonuclease, located between the clamp sections and the target specific sections, allows the Keylocks to be freed from at least their clamp sections.

Compound Probe

In certain embodiments of the present invention, a set of probes are used that is described in WO2005021794. The target sequence is brought into contact with a first and a second probe, wherein the first probe contains a first target specific section that is complementary to the target sequence and wherein the first probe preferably does not contain a first primer binding sequence in an optional first tag section. The second probe contains a second target specific section and a second tag section wherein the second tag section contains a second primer binding sequence. The second tag section may contain an identifier between the second primer binding sequence and the second target specific section. After, or simultaneously with, the hybridization and ligation of the two probes, a compound probe is provided that contains a section that is capable of hybridizing to (part of) the first target specific section of the first probe and further contains a section that contains a primer binding section. Both, the first tag section and the compound probe section that contains a primer binding site may further contain a restriction site. The restriction site in the first tag section is located between the primer binding site and the target specific section. The restriction site in the compound probe is located between the primer binding site and the section that can hybridize to the first target section. The compound probe hybridizes to the ligated first and second probe. Elongation of the compound probe along the ligated first and second probe provides for the elongated compound probe that can subsequently be amplified using first and second primers that can bind to the first and second primer binding sites. The resulting amplicons can be restricted using one or more restriction endonucleases and detected using the high throughput sequencing technologies as described herein and the target sequence in the sample can be identified by means of the presence or absence of the identifier(s) and/or locus/allele information.

Tag Section

The term tag section is used to denote those parts of the probes that are not capable of hybridizing to the target nucleotide sequences. The tag sections usually contain identifiers and primer binding sites and in some occasions, as outlined herein elsewhere, clamp sections.

Primer Binding Sequence

Primer binding sequences can be incorporated in the probes to facilitate amplification, whether linear or exponential. Primer binding sites are preferably located in other parts of the probe than in the target specific section, preferably in the tag section which is essentially non-complementary to the target sequence. Primer binding sites are capable of binding primers to initiate primer elongation or amplification. Preferably within a group of pairs of probes (for instance such as used within one sample), the primer binding sites are universal, i.e. only a predetermined group of primer binding sites are incorporated in the probe to enable multiplex primer elongation or amplification from a limited number of primers, such as primers comprising one or more selective bases at their 3' end, such as are known from AFLP (EP 0 534 858). Between groups of pairs of probes, primer binding sites may be different (i.e. have a different sequence). In certain embodiments, the Tm of primers capable of binding to the different primer binding sites may be different between groups of pairs of probes. Typically, a primer binding sequence may have a length of between 6 and 200 nucleotides, with a preference in the area between 8 and 50, more preferably between 10 and 25 nucleotides.

Hybridization

As mentioned herein before, the probes are brought into hybridizing contact with the target sequence in the sample. The pairs of oligonucleotide probes are subsequently allowed to anneal to the, preferably adjacent, complementary parts of the target sequence in the sample. Methods and conditions for specific annealing of oligonucleotide probes to complementary target sequences are well known in the art (see e.g. in Sambrook and Russel (2001) "Molecular Cloning: A Laboratory Manual (3rd edition), Cold Spring Harbor Laboratory, Cold Spring Harbor Laboratory Press). Usually, after mixing of the oligonucleotide probes and target sequences the nucleic acids are denatured by incubation (generally at between 94 degrees Celsius and 96 degrees Celsius) for a short period of time (e.g. 30 seconds to 5 minutes) in a salt buffer. The sample containing the denatured probes and target sequences is then allowed to cool to an optimal hybridization temperature for specific annealing of the probes and target sequences, which usually is about 5 degrees Celsius below the melting temperature of the hybrid between the complementary section (target section) of the probe and its complementary sequence (in the target sequence). In order to prevent a-specific or inefficient hybridization of one of the two probes of a pair, or in a sample with multiple target sequences, it is preferred that, within one sample, the sections of the probes that are complementary to the target sequences are of a similar, preferably identical melting temperature between the different target sequences present in the sample. Thus, the complementary sections of the first and second probes preferably differ less than 20, 15, 10, 5, or 2 degrees Celsius in melting temperature. This is facilitated by using complementary sections of the first and second probes with a similar length and/or similar G/C content, the complementary sections preferably differ less than 20, 15, 10, 5, or 2 nucleotides in length and their G/C contents differ by less than 30, 20, 15, 10, or 5%. Complementary as used herein means that a first nucleotide sequence is capable of specifically hybridizing to second nucleotide sequence under normal stringency conditions. A nucleotide sequence that is considered complementary to another nucleotide sequence may contain a minor amount, i.e. preferably less than 20, 15, 10, 5 or 2%, of mismatches. Alternatively, it may be necessary to compensate for mismatches e.g. by incorporation of so-called universal nucleotides, such as for instance described in EP-A 974 672, incorporated herein by reference or by incorporation of certain modified nucleotides that are capable of compensating for mismatches for instance by increasing the melting temperature or increasing specificity such as LNAs. Since annealing of probes to target sequences is concentration dependent, annealing is preferably performed in a small volume, i.e. less than 25 microliter, preferably less than 10 microliter. Under these hybridization conditions, annealing of probes to target sequences usually is fast and does not need to proceed for more than 5, 10 or 15 minutes, although longer annealing times may be used as long as the hybridization temperature is maintained to avoid a-specific annealing. Longer annealing times are more important/required for quantitative applications which rely on complete target occupation by ligation probes in order to allow monitoring or relative amounts of target sequences between samples.

In certain embodiments of the invention, excellent results have been obtained by prolonged hybridization times such as overnight hybridization or by repeated hybridization, such as 10 cycles of 1 hour. Prolonged hybridization times can be advantageous in these assays as the difference in signal due to different hybridization efficiencies is reduced and it is considered desirable to achieve complete hybridization and ligation of all probes for which a target sequence is present. Excellent results have been obtained by a combined hybridisation-ligation step using a thermostable ligase described herein. In this embodiment the hybridisation-ligation was performed by allowing the probes to hybridize during 1 hour in the presence of a thermostable ligase, followed by a denaturation step. Repeating these steps for at least 2 times provided good results. Repeating these steps 10 times provided excellent results. To avoid evaporation during denaturation and annealing, the walls and lids of the reaction chambers (i.e. tubes or microtitre wells) may also be heated to at least the same temperature as the reaction mixture which is commonly achieved by the use of commercial DNA amplification equipment or by providing a mineral oil overlay. In preferred oligonucleotide probes the length of the target-complementary section is preferably at least 15, 18 or 20 nucleotides and preferably not more than 30, 40, or 50 nucleotides and the probes preferably have a melting temperature from the target section of at least 50 degrees Celsius, 55 degrees Celsius or 60 degrees Celsius.

Ligation

The respective 5'-phosphorylated and 3'-hydroxylated ends of a pair of first and second oligonucleotide probes or of the circularizable probe of which the target specific sections are annealed essentially adjacent to each other to the complementary parts on a target sequence are connected to form a covalent bond by any suitable means known in the art. The ends of the probes may be enzymatically connected into a phosphodiester bond by a ligase, preferably a DNA ligase. DNA ligases are enzymes capable of catalyzing the formation of a phosphodiester bond between (the ends of) two polynucleotide strands bound at adjacent sites on a complementary strand. DNA ligases usually require ATP (EC 6.5.1.1) or NAD (EC 6.5.1.2) as a cofactor to seal nicks in double stranded DNA. Suitable DNA ligase for use in the present invention are T4 DNA ligase, E. coli DNA ligase or preferably a thermostable ligase like e.g. Thermus aquaticus (Taq) ligase, Thermus thermophilics DNA ligase, or Pyrococcus DNA ligase. Alternatively, chemical ligation of suitably modified polynucleotide ends may be used to ligate two oligonucleotide probes annealed at adjacent sites on the complementary parts of a target sequence. Exemplary reactive groups on modified polynucleotide ends include, but are not limited to, phosphorothioate and tosylate or iodide, esters and hydrazide, RC(O)S, RCH2S and [alpha]-haloacyl, thiophosphoryl and bromoacetamide groups, and S-pivaloyloxymethyl-4-thiothymidine. Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the invention. Detailed protocols for chemical ligation methods and descriptions of appropriate reactive groups can be found, among other places, in Xu et al., Nucleic Acid Res., 27: 875-81 (1999); Gryaznov and Letsinger, Nucleic Acid Res. 21: 1403-08 (1993); Gryaznov et al., Nucleic Acid Res. 22: 2366-69 (1994); Kanaya and Yanagawa, Biochemistry 25: 7423-30 (1986); Luebke and Dervan, Nucleic Acids Res. 20: 3005-09 (1992); Sievers and von Kiedrowski, Nature 369: 221-24 (1994); Liu and Taylor, Nucleic Acids Res. 26: 3300-04 (1999); Wang and Kool, Nucleic Acids Res. 22: 2326-33 (1994); Purmal et al., Nucleic Acids Res. 20: 3713-19 (1992); Ashley and Kushlan, Biochemistry 30: 2927-33 (1991); Chu and Orgel, Nucleic Acids Res. 16: 3671-91 (1988); Sokolova et al., FEBS Letters 232:153-55 (1988); Naylor and Gilham, Biochemistry 5:2722-28 (1966); and U.S. Pat. No. 5,476,930. Both chemical and enzymatic ligation occur much more efficient on perfectly matched probe-target sequence complexes compared to complexes in which one or both of the probes form a mismatch with the target sequence at, or close to the ligation site (Wu and Wallace, 1989, Gene 76: 245-254; Xu and Kool, supra). In order to increase the ligation specificity, i.e. the relative ligation efficiencies of perfectly matched oligonucleotides compared to mismatched oligonucleotides, the ligation is preferably performed at elevated temperatures. Thus, in certain embodiments, of the invention, a DNA ligase is employed that remains active at 50-65 degrees Celsius for prolonged times, but which is easily inactivated at higher temperatures, e.g. used in the denaturation step during a PCR, usually 90-100 degrees Celsius. One such DNA ligase is a NAD requiring DNA ligase from a Gram-positive bacterium (strain MRCH 065) as known from WO01/61033. This ligase is referred to as "Ligase 65" and is commercially available from MRC Holland, Amsterdam.

In certain embodiments, a Taq Ligase is used. In certain embodiments, the ligase is inactivated-after ligating the first and second probes. In certain embodiments, the ligated probe is denatured from the target sequence.

In certain embodiments of the present invention, the hybridization and ligation are performed in a combined step. Such a combined step of hybridization and ligation can be performed using a cyclic temperature profile and a thermo-stable ligase.

Gap Ligation

In an alternative embodiment, for instance directed to the identification of indels, the respective ends of the target complementary sections of the first and second probe may be annealed such that a gap is left. In certain embodiments, the first and second parts of the target nucleotide sequence are not located adjacent. In other words, the first and second target specific sections of the first and second probe are not hybridized to first—and second parts of the target nucleotide sequence that are located adjacent. This is fundamentally different from other varieties of this technology such as disclosed inter alia in EP 185494, U.S. Pat. No. 5,521,065, U.S. Pat. No. 5,692,223 and WO 03054311. This gap can be filled with a suitable (third) (oligo) nucleotide and ligated. Such methods are known in the art as 'gap ligation' (Illumina Golden Gate assays) and are disclosed inter alia in WO 00/77260; U.S. Pat. No. 5,185,243; EP439182; EP320308; WO90/01069. Another possibility to fill this gap is by extension of one end of the probe using a polymerase and a ligase in combination with single or multiple nucleotides, optionally preselected from A, T, C, or G, or di-, tri- or other small oligonucleotides. In case the target sequence is RNA, yet another possibility to fill the gap is by extension of one end of the probe using reverse transcriptase and a ligase in combination with single or multiple nucleotides, optionally preselected from A, T, C, or G, or di, tri- or other small oligonucleotides. Gap ligation may find application in both the detection of single SNPs/indels or multiple SNPs (haplotyping) that are closely located. In this embodiment, the sequencing step would preferably comprise the determination of the sequence of the gap.

Amplification

In the method of the invention, the ligated probes can be amplified to produce an amplified sample comprising amplified ligated probes (amplicons) that are representations of the target nucleotide sequence by any suitable nucleic acid amplification method known in the art. Nucleic acid amplification methods usually employ one or two primers, dNTPs, and a (DNA) polymerase. A preferred method for amplification is PCR. "PCR" or "Polymerase Chain Reaction" as used herein as an example of an amplification method, is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridize specifically to the target sequence prime new DNA synthesis. It is preferred that the polymerase is a DNA polymerase that does not express strand displacement activity or at least not significantly. Examples thereof are Amplitaq and Amplitaq Gold (supplier Perkin Elmer) and Accuprime (Invitrogen). One round of synthesis results in new strands of determinate length, which, like the parental strands, can hybridize to the primers upon denaturation and annealing. The second cycle of denaturation, annealing and synthesis produces two single-stranded products—that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., Current Protocols in Molecular Biology, John Wiley & Sons, Inc. (1995). Suitable conditions for the application of PCR in the method of the invention are described in EP-A 0 534 858 and Vos et al. (1995; Nucleic Acids Res. 23: 4407-4414), where multiple DNA fragments between 70 and 700 nucleotides and containing identical primer-binding sequences are amplified with near equal efficiency using one primer pair. In certain embodiments, the polymerase is inactivated after amplification. Other multiplex and/or isothermal amplification methods that may be applied include e.g. rolling circle amplification (RCA), ligase chain reaction (LCR), self-sustained sequence replication (3SR), Q-B-replicase mediated RNA amplification, or strand displacement amplification (SDA). In some instances, this may require a different design of the probes and primers without departing from the gist of the invention.

Within the present invention, amplification may be performed at several points in time. Amplification can be performed for the preparation of a library (increase in starting material for sequencing) for instance after the ligation step and/or as part of the sequencing step (i.e. emulsion PCR (Roche, Ion Torrent) or bridge amplification (Illumina).

Amplicon

Figures 2, 2A:
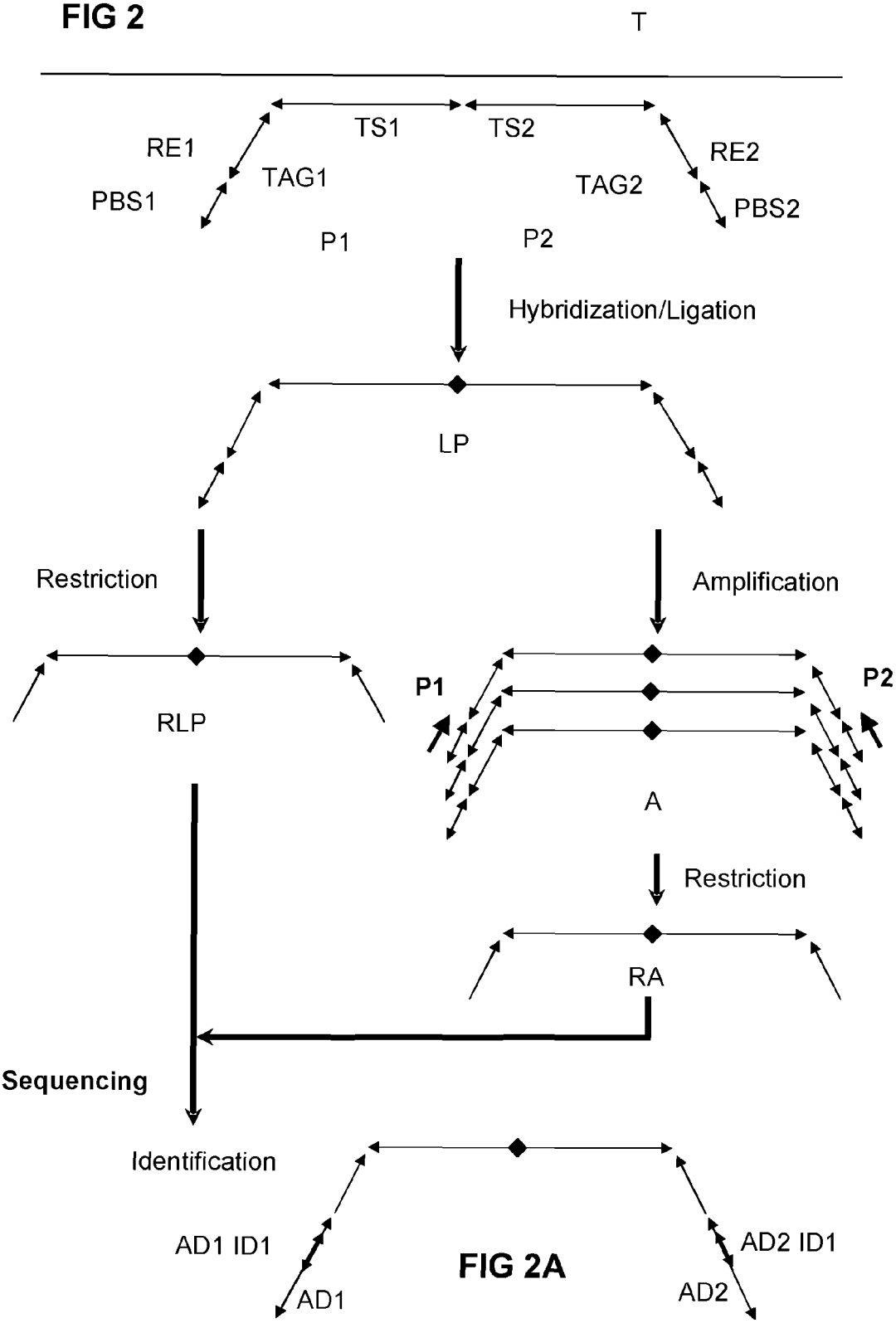
FIG. 2 illustrates, based on the probe configuration in FIG. 1B, that the two probes hybridize to the target sequence and are ligated when the hybridization is successful. Two routes now open, one in which the ligated probes (LP) are restricted by a restriction endonuclease, where necessary aided by the use of hairpin adapters or other oligonucleotides that locally provide a ds-strand that can be restricted essentially as described herein elsewhere and illustrated in FIG. 5C. The result is a Restricted ligated probe (RLP). The other route amplifies the ligated probes using one or more primers (PR1, PR2) to yield amplicons (A) that can be restricted to yield restricted amplicons (RA). To RLP and/or RA, adapters can be ligated that may contain (sample specific) identifiers. Both RLP and RA can be subjected to sequencing, resulting in identifying the presence, absence and/or amount of the target sequence in the sample. (Codominant) genotyping of the sample can then be based on the identification of the target sequence in the sample via sequence information from (part of) the target section(s) and/or identifiers provided in the tag sections.
FIG. 2A illustrates an embodiment wherein after restriction of the amplicons or ligated probes, an adapter is ligated (AD1, AD2) that may contain an identifier (AD1 ID1, AD2 ID2) which identifier may serve for instance to identify a sample origin.

The term 'amplicon' as used herein refers to the product of the amplification step of the ligated probes. The term 'amplicon' as used herein thus refers to an amplified ligated probe. After the ligation step wherein the two target specific sections are connected by mean of a ligase, the connected or ligated probe is combined with one or more primers and a polymerase and amplified to produce amplicons. The ligated probe, the primers, the polymerase and/or other parameters and variables are such that the amplification results in amplified (linear) representations of the ligated probe. Preferably an amplicon is a monomeric representation of the amplified connected probe. In certain embodiments, the amplicon comprises and preferably consists of the nucleotides of the first and optional second primer and the identifier (s) that is (are) located in-between. In certain embodiments, the amplicon may contain nucleotides from the target specific section The various embodiments of the present invention will provide further detail in this respect (FIG. 2).

Restriction Endonucleases

Restriction enzyme: a restriction endonuclease or restriction enzyme is an enzyme that recognizes a specific nucleotide sequence (target site) in a double-stranded DNA molecule, and will cleave both strands of the DNA molecule at or near every target site, leaving a blunt or a staggered end (i.e. containing an overhang of one or more nucleotides). There are also restriction endonucleases that cut ss-DNA (EndoTT, Exo I, Exo T) and they are of use in the present invention when the ligated probes are not amplified but directly cut prior to sequencing.

A Type-IIs restriction endonuclease is an endonuclease that has a recognition sequence that is distant from the restriction site. In other words, Type IIs restriction endonucleases cleave outside of the recognition sequence to one side. Examples there of are NmeAIII (GCCGAG(21/19) and FokI, AlwI, Mme I. There are Type IIs enzymes that cut outside the recognition sequence at both sides.

Frequent cutters and rare cutters are indications for restriction enzymes that typically have recognition sequences that vary in number of nucleotides from 4 (such as MseI) to 6 (EcoRI) and even 8 (NotI). The restriction enzymes used can be frequent and rare cutters. The term 'frequent' in this respect is typically used in relation to the term 'rare'. Frequent cutting endonucleases (aka frequent cutters) are restriction endonucleases that have a relatively short recognition sequence. Frequent cutters typically have 4 or 5 nucleotides that they recognise and subsequently cut. Thus, a frequent cutter on average cuts a DNA sequence every 256-1024 nucleotides. Rare cutters are restriction endonucleases that have a relatively long recognition sequence. Rare cutters typically have 6 or more nucleotides that they recognise and subsequently cut. Thus, a rare 6-cutter on average cuts a DNA sequence every 4096 nucleotides, leading to longer fragments. It is observed again that the definition of frequent and rare is relative to each other, meaning that when a 4 bp restriction enzyme, such as MseI, is used in combination with a 5-cutter such as AvaII, AvaII is seen as the rare cutter and MseI as the frequent cutter.

Isoschizomers; Isoschizomers are pairs of restriction enzymes specific to the same recognition sequence and cut in the same location. For example, Sph I (GCATG C) and Bbu I (GCATG^C) are isoschizomers of each other. The first enzyme to recognize and cut a given sequence is known as the prototype, all subsequent enzymes that recognize and cut that sequence are isoschizomers. An enzyme that recognizes the same sequence but cuts it differently is a neoschizomer. Isoschizomers are a specific type (subset) of neoschizomers.

For example, Sma I (CCC GGG) and Xma I (C CCGGG) are neoschizomers (not isoschizomers) of each other.

Restriction fragment is the term used for the DNA molecules produced by digestion of DNA with a restriction endonuclease are referred to as restriction fragments. Any given genome (or nucleic acid, regardless of its origin) will be digested by a particular restriction endonuclease into a discrete set of restriction fragments. The DNA fragments that result from restriction endonuclease cleavage can be further used in a variety of techniques such as sequencing. Restriction fragments can be blunt ended or have an overhang. The overhang can be removed using a technique described as polishing. The term 'internal sequence' of a restriction fragment is typically used to indicate that the origin of the part of the restriction fragment resides in the sample genome, i.e. does not form part of an adapter. The internal sequence is directly derived from the sample genome, its sequence is hence part of the sequence of the genome under investigation. The term internal sequence is used to distinguish over adapters, remains of recognition sequence of restriction enzymes etc.

Identifier Sequence

In certain embodiments, the oligonucleotide probe of the present invention further comprises an identifier or an identifier sequence. The identifier sequence is an oligonucleotide sequence of a variable sequence. The length of the identifier varies from 1 to 30, preferably from 2 to 20, more preferably from 3 to 10 and most preferred from 4 to 6 nucleotides. The identifier is a unique sequence. Unique as used herein means that a (combination of) identifiers unequivocally identifies a specific target sequence in a sample or a plurality of samples as different from any other target sequence, allele, locus in the sample or plurality of samples. The unique character can be explained as a ZIP-coded sequence of the type as described by Iannone et al. (2000), Cytometry 39: pp. 131-140. With an identifier of 6 nucleotides, a maximum of 4096 unique combinations can be made (=4 exp 6). In certain embodiments, the identifier contains a 2 base GC (or other defined short G/C-rich) anchor sequence at the 3' end to ensure equal binding affinity and amplification efficiency. Further it is preferred that the identifier does not contain two identical consecutive bases and it is further preferred that all identifiers used in a set of identifiers differ by at least two bases in order to ensure unequivocal sequence recognition. When multiple samples are used it is preferred that each sample can be identified using a specific set of identifiers. The identifier is generally located such that amplification or restriction of the ligated probes using the primer binding sequences and/or restriction endonucleases will incorporate the identifier to the end that the resulting amplicon or restricted ligated probe contains the identifier sequence.

Typically this means that in the ligated probe, the identifier is located near the target section and between the first primer binding site and the position of the optional second primer binding site (see FIG. 1B). In embodiments using two or more identifiers, for instance locus-allele combinations, the identifiers are also located between the primer binding sites. In certain embodiments, two identifiers can be provided, one in each probe. One of the probes can be seen as a locus probe, i.e. directed to a specified locus and contains a locus specific identifier. The other probe can be an allele-specific probe, i.e. contain a allele specific nucleotide, preferably at its point of ligation. The allele specific probe may contain a allele specific identifier. In this way the presence or absence of a specific locus-allele combination is identified by the presence/absence of the combined identifiers. When testing for all allelic variation of a polymorphisms, only one locus probe is needed, combined with 4 allele specific probes. In certain embodiments, only the allele specific probe may comprise an identifier that comprises a locus specific identifier section and an allele specific identifier section, for instance in the form of a 5 bp locus identifier, followed by a 2 bp allele identifier. Or a 5 bp sample identifier followed by a 2 bp allele identifier (in one probe or in both probes) or and part of the target section to identify the locus.

Also sample-based identifiers are possible, alone, or in combination with locus and/or allele identifiers. The sample identifiers can be provided before hand in the probe, but can also be ligated to the restricted probes or amplicons. The sample based identifiers can also be present in the adapters that are ligated to the restricted probes or amplicons.

Based on this guidance a variety of possibilities are now available to the skilled person. Thus, when multiple samples are analysed in one sequencing run, one of the identifiers can be used for the identification of the sample in the plurality of samples. For identification purposes it is also possible to use a combination of the sequence of the target specific section (identifying the locus and/or allele), one (part of the) identifier identifying the allele and/or locus and another (part of the) identifier identifying the sample.

In certain embodiments, identifiers can be used for the identification of the sample and the allele, and the locus can be identified by at least part of the sequence of the target specific section.

Summarizing, identifiers (ID) can be introduced, independently, in the tag section of the probe, in an adapter ligated to the restricted ligated probes or amplicons, introduced via a primer during an amplification step and/or in the target specific sections themselves (locus (L)/allele (Al) information). The identifiers can be positioned, independently, in the locus/allele information, between the restriction site (RE) and the allele/locus sequence (target specific sections), between the adapter that is ligated to the restricted ligated probes or restricted amplicons. Both the introduction and the position can be independently arranged in one or both probes.

Figure 3:
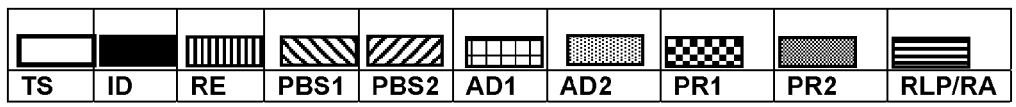
Figure 3A:
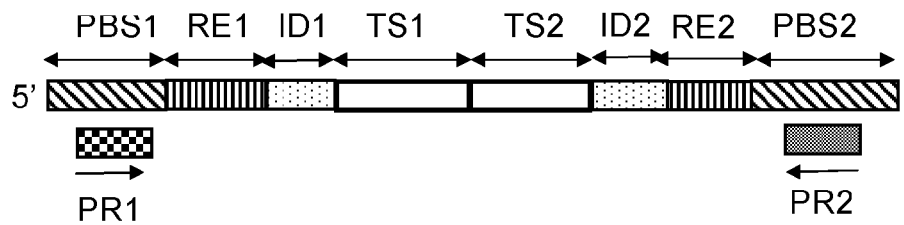
FIG. 3A illustrates a typical ligated probe according to the invention comprising primer binding sites (PBS1, PBS2), recognition sites for restriction endonucleases (RE1, RE2), Identifiers (ID1, ID2), target specific sections (TS1, TS2) and primers for amplification (PR1, PR2)
Figure 3B:
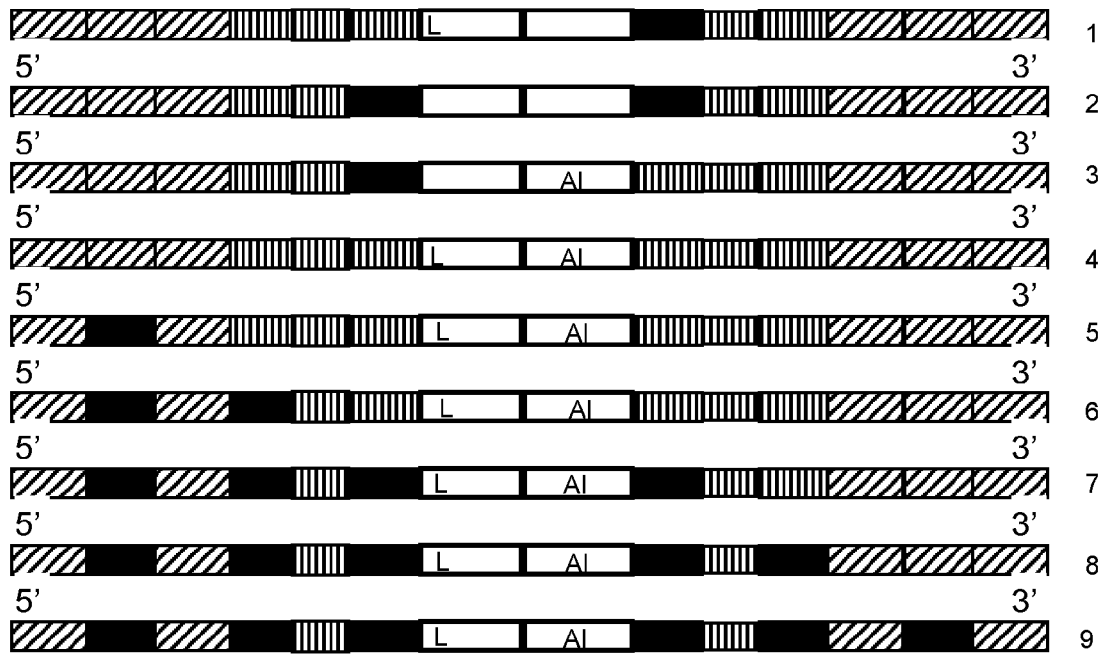
FIG. 3B illustrates a number of the various possibilities where identifiers can be located in the probes, amplicons and adapter-ligated fragments of the invention. The identifiers can be independently present, or in combination. The target specific sequence can also serve as an identifier in the sequence based method for genotyping, the Locus (L) and allele (Al) are also indicated here as possible identifiers. For example, the allele can be represented by an identifier (1) and the locus by the sequence of the target section (1). Both allele and locus can be represented by an identifier (2). Or the locus is represented by an identifier and the allele by the target specific section (3). The sample can be represented by an identifier, independently from the representation of the allele and/or locus (5). Variations 6, 7, 8, and 9 display various combinations of identifiers that may serve different or identical purposes. Other variations are possible and are equivalent with the currently displayed possibilities.

A schematic representation of some of the various individual positions of the identifiers in the (ligated) probes is provided in FIG. 3B.

In a particular preferred embodiment of the invention, the probes comprise a target section and a recognition sequence and optionally a primer binding sequence. After ligation, the ligated probes are restricted or amplified followed by restriction/digestion to give restricted ligated probes (RLP) or restricted amplicons (RA). To the resulting RLP/RA, one or two adapters are ligated that contain one or more identifiers. The resulting adapter-ligated RLP/RA are now sequenced. The allele/locus combination of the target sequence is identified by the sequence information from the target section. The sample is identified based on the identifier(s) in the ligated adapter(s). This is an efficient way of analyzing multiple target sequences in one sample, combining the results form a plurality of samples and analyze the combined samples. It is illustrated in FIG. 10.

Primers

The ligated probe is amplified using a pair of primers corresponding to the primer-binding sites. In certain embodiments, the pair of primers contains only one primer and the amplification is linear rather than exponential. In certain embodiments, the pair comprises a first primer that is capable annealing to the first primer-binding section and capable of initiating amplification or elongation. In certain embodiments, the pair further comprises a second primer that is capable annealing to the second primer-binding section and capable of initiating amplification or elongation. In certain embodiments, the second primer has the same sequence as the second primer binding site in the probe, i.e. is a reverse primer. In a preferred embodiment, at least one of the primers or the same pair of primers is used for the amplification of two or more different ligated probes in a sample, preferably for the amplification of all ligated probes in a sample. Such a primer is sometimes referred to as a universal primer as these primers are capable of priming the amplification of all connected probes containing the corresponding universal primer binding site and consequently of all ligated probes containing the universal primer binding site. The different primers that are used in the amplification in step (i) are preferably essentially equal, in annealing and priming efficiency. Thus, the primers in a sample preferably differ less than 20, 15, 10, 5, or 2 degrees Celsius in melting temperature. This can be achieved as outlined herein elsewhere for the target-specific sections of the oligonucleotide probes. Unlike the sequence of the target-specific sections, the sequence of the primers is not dictated by the target sequence. Primer sequences may therefore conveniently be designed by assembling the sequence from tetramers of nucleotides wherein each tetramer contains one A, T, C and G or by other ways that ensure that the G/C content and melting temperature of the primers are identical or very similar. The length of the primers (and corresponding primer-binding sites in the tag section of the second probe) is preferably at least 12, 15 or 17 nucleotides and preferably not more than 25, 30, 40 nucleotides. In a certain embodiment, at least two of the second oligonucleotide probes that are complementary to at least two different target sequences in a sample each comprise a tag section that comprises a primer-binding section that is complementary to a single primer sequence.

In certain embodiments, to ensure similar priming efficiency compared to other primers harboring the same anchor sequence, the primer may comprise a 3' anchoring sequence, preferably a 2 bp anchoring sequence, preferably a GC anchoring sequence. Typically, the corresponding primer binding sequence will also harbor the complement thereof.

Thus, preferably at least one of the first and second primer in a primer pair is used for the amplification of ligated probes corresponding to at least two different target sequences in a sample, more preferably for the amplification of connected probes corresponding to all target sequences in a sample. Preferably only a single first primer is used and in some embodiments only a single first and a single second primer is used for amplification of all connected (ligated) probes. Using common primers for amplification of multiple different fragments usually is advantageous for the efficiency of the amplification step. The ligated probes obtained from the ligation of the annealed probe sections are amplified, using a primer pair, preferably consisting of a pair of primers for each of the ligated probes in the sample.

The primer pair comprises primers that are complementary to primer-binding sequences that are present in the ligated probe. A primer pair usually comprises a first and at least a second primer, but may consist of only a single primer that primes in both directions. Excellent results have been obtained using primers that are known in the art as AFLP-primers such as described inter alia in EP534858 and in Vos et al., Nucleic Acid Research, 1995, vol. 23, 4407-4414 and discussed in more detail herein below.

High Throughput Sequencing

High-throughput sequencing or screening, often abbreviated as HTS, is a method for scientific experimentation especially relevant to the fields of biology and chemistry. It is sometimes also referred to as Next Generation Sequencing and is amply described in Janitz Ed. Next Generation Genome sequencing, Wiley VCH, 2008. Through a combination of modern robotics and other specialized laboratory hardware, it allows a researcher to effectively screen large amounts of samples simultaneously.

It is preferred that the sequencing is performed using high-throughput sequencing methods, such as the methods disclosed in WO 03/004690, WO 03/054142, WO 2004/069849, WO 2004/070005, WO 2004/070007, and WO 2005/003375 (all in the name of 454 Life Sciences, now Roche diagnostics), by Seo et al. (2004) Proc. Natl. Acad. Sci. USA 101:5488-93, and technologies of Helicos, Solexa, US Genomics, etcetera, which are herein incorporated by reference.

High Throughput Sequencing Based on Roche GS FLX Technologies

In certain embodiments, it is preferred that sequencing is performed using the apparatus and/or method disclosed in WO 03/004690, WO 03/054142, WO 2004/069849, WO 2004/070005, WO 2004/070007, and WO 2005/003375 (all in the name of 454 Life Sciences, now Roche Diagnostics), which are herein incorporated by reference. The technology described allows sequencing of 40 million bases in a single run and is 100 times faster and cheaper than competing technology. The sequencing technology roughly consists of 5 steps:

1) fragmentation of DNA and ligation of specific adapters to create a library of single-stranded DNA (ssDNA);
2) annealing of ssDNA to beads, emulsification of the beads in water-in-oil microreactors and performing emulsion PCR to amplify the individual ssDNA molecules on beads;
3) selection of/enrichment for beads containing amplified ssDNA molecules on their surface;
4) deposition of DNA carrying beads in a PicoTiter™ Plate; and 5) simultaneous sequencing in over 1,000,000 wells by generation of a pyrophosphate light signal. The method will be explained in more detail below.

In a preferred embodiment, the sequencing comprises the steps of:
(a) annealing adapted fragments to beads, each bead being annealed with a single adapted fragment;
(b) emulsifying the beads in water-in-oil microreactors, each water-in-oil microreactor comprising a single bead;
(c) loading the beads in wells, each well comprising a single bead; and generating a pyrophosphate signal. In the first step (a), sequencing adapters are ligated to fragments within the combination library. Said sequencing adapter may includes a further identifier and further sequences for annealing to a bead, a sequencing primer region and a PCR primer region. Thus, adapted fragments are obtained. In a first step, adapted fragments are annealed to beads, each bead annealing with a single adapted fragment. To the pool of adapted fragments, beads are added in excess as to ensure annealing of one single adapted fragment per bead for the majority of the beads (Poisson distribution). In a next step, the beads are emulsified in water-in-oil microreactors, each water-in-oil microreactor comprising a single bead. PCR reagents are present in the water-in-oil microreactors allowing a PCR reaction to take place within the microreactors. Subsequently, the microreactors are broken, and the beads comprising DNA (DNA positive beads) are enriched. In a following step, the beads are loaded in wells, each well comprising a single bead. The wells are preferably part of a PicoTiter™ Plate allowing for simultaneous sequencing of a large amount of fragments. After addition of enzyme-carrying beads, the sequence of the fragments is determined using pyrosequencing. In successive steps, the PicoTiter™ Plate and the beads as well as the enzyme beads therein are subjected to different deoxyribonucleotides in the presence of conventional sequencing reagents, and upon incorporation of a deoxyribonucleotide a light signal is generated which is recorded. Incorporation of the correct nucleotide will generate a pyrosequencing signal which can be detected.

Pyrosequencing itself is known in the art and described inter alia on www.biotagebio.com, www.pyrosequencing.com/section technology. The technology is further applied in e.g. WO 03/004690, WO 03/054142, WO 2004/069849, WO 2004/070005, WO 2004/070007, and WO 2005/003375 (all in the name of 454 Life Sciences, now Roche Diagnostics), which are herein incorporated by reference. In the present invention, the beads are preferably equipped with primer (binding) sequences and/or clamp sections or parts thereof that are capable of binding the amplicons or the ligated probes, as the case may be. In other embodiments, the probes or the primers used in the emulsion amplification are equipped with sequences that allow binding of the amplicons or the ligated probes to the beads in order to allow subsequent emulsion amplification followed by sequencing. The sequenced amplicons or ligated probes will reveal the identity of the identifier(s) and, optionally part of the target sequence and thus of the presence or absence of the target sequence in the sample.

High Throughput Sequencing Based on Illumina Genome Analyzer/HiSeq/Miseq Technologies One of the methods for high throughput sequencing is described inter alia in WO0006770, WO0027521, WO0058507, WO0123610, WO0157248, WO0157249, WO02061127, WO03016565, WO03048387, WO2004018497, WO2004018493, WO2004050915, WO2004076692, WO2005021786, WO2005047301, WO2005065814, WO2005068656, WO2005068089, WO2005078130. In essence, the method start with adapter-ligated fragments of DNA. The DNA to be used in the presently described sequencing technology is the restricted ligated probes (RLP) or restricted amplicons (RA). The adapter ligated DNA hybridizes randomly to a dense lawn of primers that are attached to a solid surface, typically in a flow cell. After elongation, the end of the newly formed fragments hybridizes to a primer that is attached to the solid support in the near vicinity of the fragment. This primer is extended in the presence of nucleotides and polymerases to provide ds-fragments The primers are extended in the presence of nucleotides and polymerases in a so-called solid-phase bridge amplification to provide double stranded fragments. Denaturation and repetition of the solid-phase bridge amplification results in dense clusters of amplified fragments distributed over the surface. The sequencing is initiated by adding four differently labeled reversible terminator nucleotides, primers and polymerase to the flow cell. After the first round of primer extension, the labels are detected, the identity of the first incorporated bases is recorded and the blocked 3' terminus and the fluorophore are removed from the incorporated base. Then the identity of the second base is determined in the same way and so sequencing continues. In the present invention, the ligated probes or the amplicons. are bound to the surface via the primer binding sequence, the primer sequence or in some embodiments, the clamp section or a combination thereof. The sequence is determined as outlined, including the identifier sequence and the associated target sequence and its presence or absence is identified.

High Throughput Sequencing Based on Ion Torrent Technologies

One of the methods for high throughput sequencing is described inter alia in US2010137143, WO2010008480, US2010282617, WO2009158006, WO2010016937, WO2010047804, US2010197507, US2010304982, WO2010138182, WO2010138186, WO2010138187, WO2010138188. The method is based on fragmenting sample DNA, ligation of adapters, generation of ss-DNA strands, capturing the strands on beads followed by emulsion PCR and subsequent annealing of an oligonucleotide to prime the synthesis of DNA. In essence it is array-based on the measurement of the proton released that occurred when two dNTPs are coupled to each other. Each time a nucleotide is added, a proton is released. Measurement of the release to the proton is a measure for the successful incorporation of the nucleotide in the oligonucleotide.

The detection of a specific nucleotide on a growing DNA strand occurs inside a fabricated well of an specific semiconductor chip. The sequencing chip captures voltage measurements from the direct release of hydrogen ions following DNA polymerization. The total number of independent measurements, or sequence reads, is a function of the number of sensors and fabricated wells that a chip contains.

Adapters

In some of the embodiments of the present invention, one or more adapters are ligated to one or both ends of the restricted amplicons or restricted ligated probes.

Adapters as used herein are short double-stranded DNA molecules with a limited number of base pairs, e.g. about 10 to about 50 base pairs in length, which are designed such that they can be ligated to the ends of restriction fragments. Adapters are generally composed of two synthetic oligonucleotides which have nucleotide sequences which are partially complementary to each other. When mixing the two synthetic oligonucleotides in solution under appropriate conditions, they will anneal to each other forming a double-stranded structure. After annealing, one end of the adapter molecule is designed such that it is compatible with the end of a restriction fragment and can be ligated thereto; the other end of the adapter can be designed so that it cannot be ligated, but this need not be the case (double ligated adapters).

Preferably the adapters are ligated prior to the sequencing step. To the restricted ligated probes or to the restricted amplicons adapters are ligated that can be used in a subsequent amplification step that is part of the sequencing step (emulsion PCR or bridge amplification), for instance to anneal to a carrier (such as a bead) used in the sequencing technology and to provide for additional functionalities that may be useful during the sequencing step, such as primer-binding sites to facilitate an amplification step as part of the sequencing protocol. Such adapters are usually referred to as 'sequencing adapters' and their design and functionality will be exemplified herein below. Examples of such sequencing adapters are known in the art as P5 and P7 adapters and are used in the Illumina technology. Other technologies employ conceptually similar adapters.

Thus, in certain embodiments a (double stranded) adapter is ligated to the end of the restriction fragment provided by the restriction endonuclease. The adapter is constructed such that it is ligatable to the end of the restriction fragment. If the end of the restriction fragment is blunt ended, either by polishing or by the endonuclease, the adapter is preferably also blunt ended. The adapter may be constructed or designed such that only one strand is ligatable to the restriction fragment end whereas the other strand of the adapter may be designed such that it does not ligate, for instance via the use of a non-phosphorylated nucleotide. If the end of the restriction fragment is staggered, it is preferred to use a staggered adapter that preferably contains at least one ligatable end. A ligatable end in this context is an end that is at least complementary to the remains of the restriction site of the restriction endonuclease. If one restriction enzyme is used on the ligated probes or on the amplified ligated probes, one adapter can be used. It is also possible to use multiple adapters when one restriction enzyme is used on the ligated probes or on the amplified ligated probes. The use of multiple adapters may provide an additional functionality, for instance in separating (selecting) part of the ligated probes or on the amplified ligated probes as part of a complexity reduction. In certain embodiments, when two (a first and a second) restriction endonucleases are used, two (a first and a second) adapter can be ligated to the respective ends of the restriction fragments.

In certain embodiments, the adapter can be a Y-shaped adapter (sometimes called a 'forked adapter'). A Y shaped adapter can have a staggered or a blunt end. In general, a Y shaped adapter is made from two single stranded DNA fragments. The two fragments of single stranded DNA each contain a section at one end of the strand that is complementary to each other, such that the sections are capable of annealing the two strands to each other. The fragments of single stranded DNA each contain a further section that is non complementary to each other and that do not anneal. The complementary end allows to the Y-shaped adapter to ligate to the ends of the restricted amplicons or restricted ligated probes. The complementary end may be of any suitable length and can be from 1-50 nucleotides in length. The use of a Y shaped adapter allows the introduction of two different strands of DNA using only one type of adapter. A schematic representation thereof is given in FIG. 5A The adapters can further contain identifiers and the Y shaped adapter can contain different identifiers in the two arms of the Y shaped adapter.

In certain embodiment, the Y shaped adapter can be designed such that one Y shaped adapter is capable of ligating to both strands of a restriction fragment while at the same time avoiding the self-ligation of the Y shaped adapter. In this embodiment, the overhang of the restriction fragment is partly filled prior to the ligation step, thereby allowing the Y shaped adapter to only ligate to the fragment and not to other Y shaped adapters. A schematic representation thereof is given in FIG. 5B As an alternative, adapters can also be of the type known as 'hairpin adapters' which are capable of annealing and ligating to single strand DNA, providing partly double stranded DNA.

In another embodiment relating to the use of singe stranded ligated probes in the step where the ligated probes are restricted prior to the sequencing step, the use of single stranded cutting nucleases is contemplated. As an alternative, an oligonucleotide that will provide a local ds-strand that subsequently can be cut using the restriction endonuclease can be provided. Adapters can also be of the type known as 'hairpin adapters' which are capable of annealing and ligating to single strand DNA, providing partly double stranded DNA that can subsequently be cut with an endonuclease. A schematic representation of the last two variants is given in FIG. 5C.

The currently described sequencing technologies contain some variations in their sequencing protocols. The use of these sequencing variations can have influence on the design of the various probes and primers used in the present invention, the way in which the sequence data is obtained and the quality, reliability and amount of data generated.

Unidirectional Single Read Sequencing

With single read sequencing, the restricted ligated probe or restricted amplicon is ligated to one or two adapters (sequencing adapters) and sequenced in one direction using one primer. The nucleotide sequence that is ultimately subjected to sequencing is commonly indicated in this description as the 'sequencing fragment'.

This embodiment is schematically depicted in FIG. 4A. In this embodiment, the sequencing adapter-ligated fragment is sequenced starting from the primer (sequencing primer, SEQ PR) into the fragment, thereby sequencing at least part of the tag section that remained after restriction, at least part of the target sequence (i.e. the target specific sections). Any identifier located 3' of the sequencing primer will be sequenced along as will (part of) the target sequence. This identifier may be present in the sequencing adapter and/or in the tag section that remained after restriction. The target sequence can then be identified by the identifier(s) or the target sequence or a combination thereof.

Unidirectional Single Read Double Tagging Sequencing

With unidirectional single read double tagging, (unidirectional single read double priming) the restricted amplicon or restricted ligated probe is ligated to one or two sequencing adapters and sequenced in one direction but with two primers (SEQ PR1, SEQ PR2). This embodiment is schematically depicted in FIG. 4B. In this embodiment, identical to the single read sequencing, the sequencing fragment is sequenced starting from the sequencing primer SEQ PR1 into the fragment, thereby sequencing at least part of the tag section that remained after restriction, at least part of the target sequence (i.e. the target specific sections). In this embodiment, the sequence read resulting from this step is indicated as the 'long read'. The second primer (SEQ PR2)

is directed to a second part of the sequencing adapter(s)-ligated restricted ligated probe or restricted amplicon and amplifies a second part thereof, typically indicated as the 'short read'.

When re-clustering of the sequencing fragments for sequencing is performed, the second sequencing primer, may also result in a long read (See FIG. 4C). In re-clustering, the sequencing fragments are subjected to a protocol in which they are annealed to the carrier using the other sequencing adapter (resulting in a bridge of the sequencing fragment on the carrier and subsequent dis-annealing of the first sequencing adapter for the carrier in which they were hybridised and annealed). The result is that the orientation of the fragment vis-à-vis the carrier is shifted (re-clustered) and sequencing can be performed again. An example of such re-clustering and sequencing from both sides (paired end sequencing) is described in Bentley et. Nature 2008, 456, 53-59. Having performed a re-clustering may hence lead to two long reads (Long1, Long 2).

Bidirectional Double Tagging Sequencing

With bidirectional double tagging sequencing (bidirectional double priming sequencing), depicted in FIG. 4D, the sequencing fragment is sequenced using paired-end sequencing wherein the fragment is sequenced from both sides.

In this embodiment, a third identifier can be present in the sequencing fragment which can be addressed by using a primer that has a reverse orientation that can result a second long read (Long 2). The third identifier can be addressed (sequenced) by the second primer or a third primer that is specifically directed to identify the third identifier (exemplified in the figure by a different overlap, but this need not be the case). In a further embodiment, the primer with the reverse orientation is not used to identify the identifier, so the third identifier can be omitted and the sequencing step in the reverse direction serves to provide sequence data of the sequencing fragment.

Paired End Sequencing

As used herein, 'paired-end sequencing' is a method that is based on high throughput sequencing, particular based on the platforms currently sold by Illumina and Roche. Illumina has released a hardware module (the PE Module) which can be installed in the existing sequencer as an upgrade, which allows sequencing of both ends of the template, thereby generating paired end reads. It is in particular preferred to use paired end sequencing, in particular using Roche or Illumina technology, in the methods according to the current invention. Examples of paired end sequencing are described for instance in US20060292611 and in publications from Roche (454 sequencing).

Mate Pair Sequencing

Mate pair sequencing is a paired end sequencing variant wherein the ends are mated. DNA fragments that are to be sequenced, such as restriction endonuclease-treated ligation products (or amplicons there from) are circularised, fragmented and the fragments that contain the ends of the original DNA are subsequently sequenced thereby obtaining sequence information from both ends of the original DNA in one sequencing step. Mate pair sequencing can be applied to any of the sequencing fragments that are described herein. See also www.illumina.com for examples of mate pair sequencing.

Detailed information on the concept of mate pair sequencing is provided in FIG. 6. As an example one of the ligation products is used, but the principle of mate pair sequencing applies to any of the sequencing fragments of the present invention, regardless of the elements present in the sequencing fragments. To illustrate this, a sequencing fragment is generalised into one solid line that represents a DNA sequencing fragment. The fragment is circularised, and fragmented (via shearing or restriction). To the ends of the fragment sequencing adapters are ligated and the resulting DNA strand is subjected to sequencing, preferably from both (paired) ends.

Throughout this specification, figures and the appended claims the notions 'first' and 'second' are used to distinguish between elements such as the probes, adapters, primers etc. used in the assay and their respective components. The notions "first" and "second" are not used herein as summations, i.e. it is not so that there can only be a second component when there is also a first component. For reasons of consistency and ease of reference these notions are also used when the embodiment itself does not constitute of two probes or of two components. For instance, a circularizable probe, being only one probe, still contains a first and second target specific section. Likewise, In FIG. 1, for instance either one of the first and second probe may contain an identifier. In case of the first probe this is depicted as the first identifier and in case of the second probe this is depicted as the second identifier. In case the second probe contains an identifier and the first probe does not, this identifier may referred to in this application as the second identifier without implicating the existence of a first identifier.

Example Single Nucleotide Polymorphism (SNP) Detection in Melon

1. DNA Isolation

Genomic DNA of two F2 off spring of a *Charantais* melon segregating population, was isolated from leaf material using a modified CTAB procedure described by Stuart and Via (Stuart, C. N., Jr and Via, L. E. (1993) A rapid CTAB DNA isolation technique useful for RAPD fingerprinting and other PCR applications. Biotechniques, vol. 14, 748-750). DNA samples were diluted to a concentration of 100 ng/µl in TE (10 mM Tris-HCl pH 8.0, 1 mM EDTA) and stored at −20° C.

2. DNA Amplification

In order to have enough DNA available for multiple tests, the isolated DNA was amplified using the Illustra GenomiPhi v2 DNA Amplification kit (GE Healthcare) according to the manufacturer's specifications.

3. Selection of Melon SNPs

Melon SNPs were selected from a collection that had previously been incorporated into BeadXpress assays (Illumina) and used to genotype several of the above mentioned samples. A total of 23 SNPs was selected containing a wide variety of SNPs, see table 1 The SNPs serve as exemplary and do not limit the general concept of the technology of the invention

TABLE 1

Selected Melon SNPs:

| SNP | SNP | Alleles |
|---|---|---|
| 1 | SBG0004r | A/G |
| 2 | SBG0005 | T/C |
| 3 | SBG0008 | A/G |
| 4 | SBG0009 | C/G |
| 5 | SBG0010 | C/T |
| 6 | SBG0013 | A/C |
| 7 | SBG0014 | A/C |
| 8 | SBG0015 | A/T |
| 9 | SBG0016 | T/G |
| 10 | SBG0018 | T/C |
| 11 | SBG0021 | C/G |

TABLE 1-continued

Selected Melon SNPs:

| SNP | SNP | Alleles |
|---|---|---|
| 12 | SBG0022 | A/G |
| 13 | SBG0023 | T/C |
| 14 | SBG0025 | A/G |
| 15 | SBG0026 | T/C |
| 16 | SBG0027 | T/C |
| 17 | SBG0028 | T/C |
| 18 | SBG0030 | A/T |
| 19 | SBG0033 | T/C |
| 20 | SBG0036 | T/C |
| 21 | SBG0037 | T/C |
| 22 | SBG0039 | A/G |
| 23 | SBG0040 | A/T |

4. Oligonucleotide Probe Design for Oligonucleotide Ligation Reaction

The oligonucleotide probes (5'-3' orientation) were designed using common procedures based on the known sequence of the loci and selected to discriminate the SNP alleles for each of the 23 loci described in Table 1. PCR primer binding regions were included. All probes were phosphorylated at the 5' end. For each SNP, two allele probes were designed containing the specific allele and one reverse probe. Phosphorylation of the reverse probes is functional, whereas phosphorylation of the allele specific probes is merely a result of cost reduction.

All oligonucleotides were purchased from Metabion, Martinsried, Germany. The concentration of the oligonucleotides was adjusted 1 µM.

A 4× Probe mix was prepared by combining 1 µl of each Allele probe (=46×) and 2 µl of each Reverse probe (=23×). The 4× Probe mix was 4× diluted with MilliQ water to obtain a 1× Probe mix.

5. Design of the PCR Amplification Primers

The sequences of the primers used for PCR amplification of the Oligonucleotide ligation products were complementary to the PCR primer binding regions incorporated in the ligation probes described in "4. Oligonucleotide Probe Design for Oligonucleotide ligation Reaction". The PCR primer sequences are derived from the adapter sequences used in the AFLP process as described by Zabeau & Vos, 1993: Selective restriction fragment amplification; a general method for DNA fingerprinting. EP 0534858-A1, B1; U.S. Pat. No. 6,045,994) and Vos et al (Vos, P., Hogers, R., Bleeker, M., Reijans, M., van de Lee, T., Hornes, M., Frijters, A., Pot, J., Peleman, J., Kuiper, M. et al. (1995) AFLP: a new technique for DNA fingerprinting. Nucl. Acids Res., 21, 4407-4414). Specifically, the 3' end of the primer sequences were modified to harbor a part of the restriction enzyme recognition site for EcoRI (allele specific probe) or HindIII (reverse (=locus specific) probe).

6. Buffers and Reagents

The concentration of the buffers was: Multiplex Oligonucleotide Ligation Buffer (10×): 200 mM Tris-HCl pH 7.6, 250 mM KAc, 100 mM MgAc, 10 mM NAD, 100 mM Dithiothreitol, 1% Triton-X100. PCR buffer (10×): 100 mM Tris-HCl pH 8.3, 500 mM KCl, 15 mM MgCl2, 0.01% (w/v) gelatin. Restriction Ligation Buffer (5×): 5× DNase buffer (Affymetrix), 25 mM Dithiothreitol, 250 µg/ml BSA. Minelute elution buffer including Tween: 10 mM Tris pH 8.5, 0.1% Tween X-100.

7. Multiplex Oligonucleotide Ligation Reaction and Amplification

Ligation reactions were carried out in duplicate for each of the two isolated DNA samples as follows: 100 to 200 ng (amplified) genomic DNA was combined with 1 µl 10× Multiplex Oligonucleotide Ligation Buffer, 4 units Taq DNA ligase (New England BioLabs), 0.4 µl 1× Probe mix and MilliQ water to a total of 10 µl. The reaction mixture was incubated for 2 minutes at 94° C. follow by 4 hours at 60° C. Reactions were kept at 4° C. until further use. Ligation Reactions were 4× diluted with 1× Multiplex Oligonucleotide Ligation Buffer. Amplification of the ligation products was carried out as follows: 10 µl 4× diluted ligation reaction, 30 ng of each primer (E00LF and H00LR), 0.2 µl 20 mM mixture of each dNTP, 2 µl of 10×PCR buffer, 0.4 units AmpliTaq-Gold (Applied Biosystems) and MilliQ water to a total of 20 µl. Amplification reactions were setup in duplicate. The thermocycling profile was performed on a PE9700 (Perkin Elmer Corp.) with a gold or silver block using the following conditions: Step 1: Pre PCR incubation: 12 minutes at 94° C. Step 2: Denaturation: 30 seconds at 94° C.; Annealing; 30 seconds at 65° C. in the first cycle. In each next cycle this annealing temperature was lowered by 0.7° C. Extension: 1 minute extension at 72° C. Total cycle number is 13 Step 3: Denaturation: 30 seconds at 94° C. Annealing; 30 seconds at 56° C. Extension: 1 minute extension at 72° C. Total cycle number is 23

Step 4: Extension: 7 minutes at 72° C. Reactions were kept at 4° C. until further use.

Amplification products (20 µl) were purified using MinElute kit (Qiagen) and eluted in 10 µl MilliQ water.

8. Restriction Ligation Reaction

Amplification products of step 7 (7 µl) were digested with the restriction enzymes EcoRI (20 units) and HindIII (20 units) in a total volume of 40 µl containing 1× Restriction Ligation Buffer and incubation at 37° C. for 2 hour.

Adapters were ligated to the digestion products through addition of 5 pmol of generic HindIII adapter, 5 pmol EcoRI adapter containing sample ID, 0.1 µl 100 mM ATP, 2 µl 5× Restriction Ligation Buffer, 1 unit of T4 DNA ligase in a total volume of 10 µl and incubation at 37° C. for 3 hours.

The sequence composition of the EcoRI adapter containing a sample ID was such that the top strand contained a 3'-located sample ID (5 nt) and the bottom strand contained a 5' located sample ID (5 nt) which were in reverse complement of the corresponding top strand.

The sample IDs differed between sample 1 and sample 2.

The 3' end of the bottom strand adapter was modified with an amino group.

The adapters were prepared by mixing equal amounts (pmol) of each oligo (top and bottom) into an eppendorf tube. Final concentration of the adapters was 50 µM.

The sequence composition of the HindIII adapter was designed and synthesized analogously to the EcoRI adapter, with and without an identifier.

9. Amplification of the Restriction Ligation Products

Restriction Ligation products were 10× diluted in MilliQ water. Five µl 10× diluted Restriction Ligation product was mixed with 5 ng forward primer, 30 ng reverse primer, 0.2 20 mM of each dNTP, 2 µl 10×PCR buffer, 0.08 µl 5 U/µl AmpliTaq DNA polymerase (Applied Biosystems) and 12.02 µl MilliQ water. The reaction mixture was placed in a ThermoCycler (PE9700, gold or silver block) and the following profile was applied: Pre incubation: 2 minutes 72° C., Cycling 50 times: 30 seconds 94° C., 2 minutes 58° C., 2 minutes 72° C. From each amplification reaction 5 µl was pooled of which 130 µl was purified using a Minelute column (Qiagen). The purified product was eluted in 30 μl Elution Buffer with Tween addition.

10. Sequencing of the Amplification Products

Sequencing of the amplified products of step 9 was performed on the Genome Analyzer II (Illumina) which is a Sequencing-by-Synthesis platform and uses the Clonal Single Molecule Array (CSMA™) technology using different sequencing protocols including unidirectional single read sequencing, unidirectional single read double tagging sequencing, bidirectional double tagging sequencing, paired end sequencing and mate pair sequencing 11. Data Processing and Genotype Determination The obtained sequence reads were screened for the presence of the identifiers, A total of 1,644,183 reads remained. All ID tags were detected with an average number of reads per sample of 411,046. The number of reads per sample varied from 308,105 (Sample 1) to 603,889 (Sample 3). Additional quality control was performed on the reads containing the sample ID tags. This included the presence of the EcoRI recognition site, absence of reads containing homopolymers (defined as contiguous stretches of the same nucleotide over more than 20 positions), the absence of reads with positive match against the NCBI chloroplast database, the absence of reads containing 'N' in the sequence and the absence of reads with low quality score (average QS<15) in the first 50 nucleotides of the read. The number of reads removed per sample varied from 12,445 (Sample 4) to 28,447 (Sample 1), with an average of 18,769. The number of reads removed per sample accounted for a small percentage of the total number of reads (average of 4.6%). As a consequence, the average percentage of reads passing the quality control filters was high (95.4%). The reads passing the quality control were used as input for determining the genotypes of the samples for each of the SNPs. This process involved aligning the reads to the reference sequences of the loci using the BWA software, processing the output with SAMtools (including sorting, merging and indexing), determining the occurrences of the alleles in the samples and determining genotypes for each sample based on the ratios of the allele occurrences. SAMtools is available through http://samtools.sourceforge.net. When a degenerate position in the reference sequences was present, an alphabetic sort for the base was used to replace the ambiguous position.

SNPs were detected in all of the 23 targets and genotypes were called, using all types of sequencing.

12. Genotype Validation

Comparison of the generated genotypes from the duplicates (Sample 1 and 2, Sample 3 and 4) and from the different sequencing protocols showed that 100% of the genotypes called were identical between the duplicates.

The genotypes determined in step 11 were compared to available genotypes which were generated using the BeadXpress technology (Illumina). Results from the comparison showed that:

21 of the SNPs loci showed 100% correlation between the current approach and the BeadXpress data.

1 SNP locus (SBG0014) was not scored in the BeadXpress data set, i.e. U (=unknown) scores, whereas the in this experiment used approach generated a clear genotype.

1 SNP locus (SBG0039) showed consistently a homozygous (current approach) versus heterozygous (BeadXpress) discrepancy.

The invention claimed is:

1. A method for determining at least one target nucleotide sequence in a sample comprising:
    (a) providing for each target nucleotide sequence a first probe and a second probe,
        wherein the first probe comprises a first target specific section and a first tag section that is non-complementary to the target nucleotide sequence and that optionally comprises a first primer binding sequence, wherein the first tag section comprise a first recognition sequence for a first restriction endonuclease;
        wherein the second probe comprises a second target specific section and a second tag section that is non-complementary to the target nucleotide sequence and that comprises an optional second primer binding sequence, wherein second tag section comprises an optional second recognition sequence for a second restriction endonuclease;
    (b) allowing the first and second target specific section of the respective first and second probe to hybridize to the target sequence;
    (c) ligating the first and second probe when the respective target specific sections of the probes are hybridized to essentially adjacent sections on the target sequence to provide ligated probes;
    (d) optionally amplifying the ligated probes with an optional first and/or an optional second primer to provide amplicons;
    (e) restricting the ligated probes or amplicons with the first and/or second restriction endonuclease to provide restricted ligated probes or restricted amplicons, and ligating a first and/or a second adapter comprising an adapter-based identifier to the restricted ligated probes or restricted amplicons;
    (f) subjecting the adapter-ligated restricted ligated probes or adapter-ligated restricted amplicons to a high throughput sequencing to determine at least part of the target nucleotide sequence and the adapter-based identifier contained in the adapter-ligated restricted ligated probes or adapter-ligated restricted amplicons;
    (g) dominant or co-dominant genotyping using the adapter-based identifier.

2. The method according to claim 1, wherein the first target specific section is located at 3'-end of the first probe and wherein the second target specific section is located at 5'-end of the second probe.

3. The method according to claim 1, wherein a first probe-based identifier sequence is located in the first tag section.

4. The method according to claim 1, wherein a second probe-based identifier sequence is located in the second tag section.

5. The method according to claim 1, wherein the first probe-based identifier is located between the first recognition sequence for a restriction endonuclease and the first target specific section.

6. The method according to claim 1, wherein the second probe-based identifier is located between the optional second recognition sequence for a restriction endonuclease and the second target specific section.

7. The method according to claim 1, wherein the first and the second tag section both comprise a recognition site for a restriction endonuclease.

8. The method according to claim 1, wherein the hybridization, ligation and an optional gap filling are performed in a combined step.

9. The method according to claim 1, wherein the recognition sequence for the restriction endonuclease for the first tag section has a different nucleotide sequence compared to the recognition site for the restriction endonuclease for the second tag section.

10. The method according to claim 1, wherein the high throughput sequencing comprises a sequencing by synthesis.

11. The method according to claim 1, wherein the high throughput sequencing comprises a bridge amplification or emulsion amplification.

12. The method according to claim 1, wherein the high throughput sequencing comprises an unidirectional single read sequencing.

13. The method according to claim 1, wherein the high throughput sequencing comprises an unidirectional single read double priming sequencing.

14. The method according to claim 1, wherein the high throughput sequencing comprises a bidirectional paired end sequencing.

15. The method according to claim 1, wherein the high throughput sequencing comprises a mate pair sequencing.

16. The method according to claim 1, wherein a plurality of target sequences is determined in one sample.

17. The method according to claim 1, wherein one target sequence is determined in a plurality of samples.

18. The method according to claim 1, wherein a plurality of target sequences is determined in a plurality of samples.

19. The method according to claim 1, wherein the probes are circularizable probes, keylock probes and/or compound probes.

20. A method for genotyping a biological sample for presence, absence or amount of a target sequence in the biological sample using an oligonucleotide ligation assay comprising at least two probes, wherein at least one of the probes comprises a recognition sequence for a restriction endonuclease in addition to a target specific section hybridizable to the target sequence, the method comprising:
(a) ligating the two probes when they are hybridized to the target sequence to obtain a ligated probe, wherein the ligated probe is restricted with a restriction endonuclease to obtain a restricted ligated probe or is amplified and restricted to obtain a restricted amplicon,
(b) ligating at least one adapter that comprises an identifier to the restricted ligated probe to obtain an adapter-ligated restricted ligated probe or to the restricted amplicon to obtain an adapter-ligated restricted amplicon, and
(c) sequencing at least part of the target sequence contained in the adapter-ligated restricted ligated probe or the adapter-ligated restricted amplicon and dominant or co-dominant genotyping using the adapter-based identifier.

21. The method according to claim 20, wherein the genotyping is co-dominant genotyping comprising at least two allele-specific probes.

22. An oligonucleotide ligation assay method comprising:
(a) hybridizing a first probe and a second probe to a target nucleotide sequence of a sample, wherein:
(i) the first probe comprises a first target specific section complementary to a first part of the target nucleotide sequence, and a first tag section that is non-complementary to the target nucleotide sequence and that comprises a first primer binding sequence and a first restriction recognition sequence; and
(ii) the second probe comprises a second target specific section complementary to a second part of the target nucleotide sequence, and a second tag section that is non-complementary to the target nucleotide sequence and that comprises a second primer binding sequence and a second restriction recognition sequence;
(b) ligating the first and second probe when the respective target specific sections of the probes are hybridized to essentially adjacent sections on the target sequence to provide ligated probes;
(c) restricting the ligated probes to provide restricted ligated probes, or amplifying and restricting the ligated probes to provide restricted amplicons;
(d) ligating a first and/or a second adapter comprising an adapter-based identifier to the restricted ligated probes or restricted amplicons;
(e) subjecting the adapter-ligated restricted ligated probes or adapter-ligated restricted amplicons to a high throughput sequencing to determine at least part of the target nucleotide sequence and the adapter-based identifier contained in the adapter-ligated restricted ligated probes or adapter-ligated restricted amplicons; and
(f) dominant or co-dominant genotyping using the adapter-based identifier.

* * * * *